(12) United States Patent
McCarthy et al.

(10) Patent No.: US 10,383,850 B2
(45) Date of Patent: Aug. 20, 2019

(54) INDAZOLE AND INDOLE DERIVATIVES AS INHIBITORS OF RETINOIC ACID RELATED ORPHAN RECEPTOR GAMMA (ROR GAMMA) FOR THE TREATMENT OF IMMUNE-RELATED DISEASES

(71) Applicant: ORCA PHARMACEUTICALS LIMITED, Abingdon (GB)

(72) Inventors: Clive McCarthy, Abingdon (GB); Naomi Went, Abingdon (GB); Roine Inge Olsson, Mölndal (SE)

(73) Assignee: ORCA PHARMACEUTICALS LIMITED, Abingdon (GB)

( * ) Notice: Subject to any disclaimer, the term of this patent is extended or adjusted under 35 U.S.C. 154(b) by 18 days.

(21) Appl. No.: 15/521,397

(22) PCT Filed: Oct. 23, 2015

(86) PCT No.: PCT/GB2015/053183
§ 371 (c)(1),
(2) Date: Apr. 24, 2017

(87) PCT Pub. No.: WO2016/063080
PCT Pub. Date: Apr. 28, 2016

(65) Prior Publication Data
US 2017/0305915 A1 Oct. 26, 2017

(30) Foreign Application Priority Data
Oct. 24, 2014 (GB) .................................. 1419015.1

(51) Int. Cl.
| | | |
|---|---|---|
| *A61K 31/404* | (2006.01) | |
| *A61K 31/405* | (2006.01) | |
| *A61K 31/416* | (2006.01) | |
| *A61K 31/437* | (2006.01) | |
| *A61K 31/4439* | (2006.01) | |
| *A61K 31/519* | (2006.01) | |
| *A61K 9/00* | (2006.01) | |
| *C07D 209/10* | (2006.01) | |
| *C07D 209/12* | (2006.01) | |
| *C07D 231/56* | (2006.01) | |
| *C07D 401/04* | (2006.01) | |
| *C07D 471/04* | (2006.01) | |
| *C07D 487/04* | (2006.01) | |

(52) U.S. Cl.
CPC .......... *A61K 31/405* (2013.01); *A61K 9/0053* (2013.01); *A61K 31/404* (2013.01); *A61K 31/416* (2013.01); *A61K 31/437* (2013.01); *A61K 31/4439* (2013.01); *A61K 31/519* (2013.01); *C07D 209/10* (2013.01); *C07D 209/12* (2013.01); *C07D 231/56* (2013.01); *C07D 401/04* (2013.01); *C07D 471/04* (2013.01); *C07D 487/04* (2013.01)

(58) Field of Classification Search
CPC combination set(s) only.
See application file for complete search history.

(56) References Cited

U.S. PATENT DOCUMENTS

2010/0016371 A1 * 1/2010 Giblin .................. C07D 209/08
514/339

FOREIGN PATENT DOCUMENTS

| EP | 1837329 A1 | 9/2007 |
|---|---|---|
| WO | 2012106995 A1 | 8/2012 |
| WO | 2014145051 A1 | 9/2014 |
| WO | 2015087234 A1 | 6/2015 |
| WO | WO-2015087234 A1 * | 6/2015 ........... C07D 231/56 |

OTHER PUBLICATIONS

Hall et al. "Discovery of a novel indole series of EP1 receptor antagonists by scaffold hopping." Bioorg. Med. Chem. Lett. 2008, 18, 2684-2690 (Year: 2008).*
PCT/GB2015/053183—International Search Report and Written Opinion dated Apr. 28, 2016.
Burris, et al., "Targeting Orphan Nuclear Receptors for Treatment of Metabolic Diseases and Autoimmunity", 2012, Chemistry & Biology 19(1):51-59.

* cited by examiner

*Primary Examiner* — Amanda L Aguirre
(74) *Attorney, Agent, or Firm* — Saul Ewing Arnstein & Lehr LLP; Domingos J. Silva

(57) ABSTRACT

The present invention provides compounds of formula (I), wherein $A^1$, $A^2$, $Z^1$, $Z^2$, $Z^3$, $R^1$, $R^2$, $R^3$, $R^4$, $R^5$, $R^6$, n, p and q are as defined herein. In certain embodiments, the compounds of the invention are RORγt antagonists. In other embodiments, the compounds of the invention are useful in the treatment and/or prevention of inflammatory and auto-immune conditions.

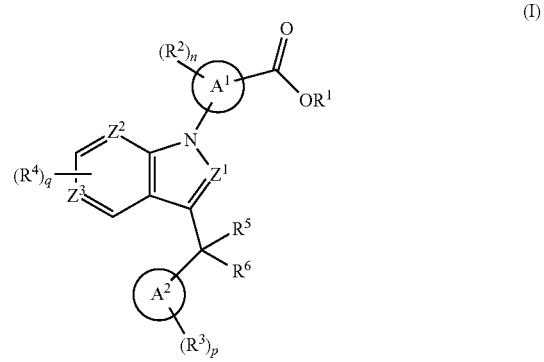

14 Claims, No Drawings

INDAZOLE AND INDOLE DERIVATIVES AS INHIBITORS OF RETINOIC ACID RELATED ORPHAN RECEPTOR GAMMA (ROR GAMMA) FOR THE TREATMENT OF IMMUNE-RELATED DISEASES

CROSS-REFERENCE TO RELATED APPLICATIONS

The present application is a 35 U.S.C. § 371 national phase application from, and claims priority to, International Application No. PCT/GB2015/053183, filed Oct. 23, 2015, and published under PCT Article 21(2) in English, which claims priority to GB Application No. 1419015.1, filed Oct. 24, 2014, all of which applications are incorporated herein by reference in their entireties.

The present invention relates to compounds which are inhibitors of retinoic acid-related orphan receptor γt (RORγt) activity and which are therefore of use in the treatment of immune-mediated diseases, including autoimmune diseases, and inflammatory conditions. The invention also relates to methods of preparing the compounds and pharmaceutical compositions containing them.

RORγt is known to play a central role in immune system development since it both regulates development of T cells in the thymus and differentiation of effector T cells in the periphery. RORγt is also required for the differentiation of pro-inflammatory Th17 cells (Ivanov et al, *Cell*, 126, 1121-1133, 2006). Small molecule inhibitors of RORγt inhibit the differentiation of human Th17 cells in vitro and reduce Th17 cell numbers and disease activity in animal models of autoimmune disease (Huh et al., 2011, *Nature* 472:486-490). RORγ is also involved in the development of other pathogenic immune cells include type 3 innate lymphoid cells (ILCs). Interleukin 23 activates ILCs in a RORγt-dependent manner (Luci et al., 2008; Buonocore et al., 2010, *Nature* 464:1371-1375) and these cells contribute to experimental colitis and are present in the inflamed intestine of patients with IBD (Buonocore et al., 2010; Geremia et al., 2011, *J Exp Med* 208:1127-1133).

It has been demonstrated that Th17 cells and their products, IL17A, IL-17F, IL-21 and IL-22, are associated with the pathology of various inflammatory and autoimmune disorders, in particular, chronic inflammatory diseases such as psoriasis, rheumatoid arthritis, multiple sclerosis, inflammatory bowel diseases, ankylosing spondylitis, systemic lupus erythematosus and lung diseases including severe asthma, chronic obstructive pulmonary disease and cystic fibrosis.

Some antagonists of RORγt are known and, for example, WO 2012/106995A1, WO 2014/026327, WO 2014/026328, WO 2014/026329, WO 2014/026330, WO 2014/028589, WO 2014/028592, WO 2014/028597 and WO 2014/028600 all relate to compounds which are said to have RORγt inhibiting activity.

The present invention relates to novel antagonists of RORγt which are of use in the treatment and prevention of these and related conditions.

In the present invention there is provided a compound of general formula (I):

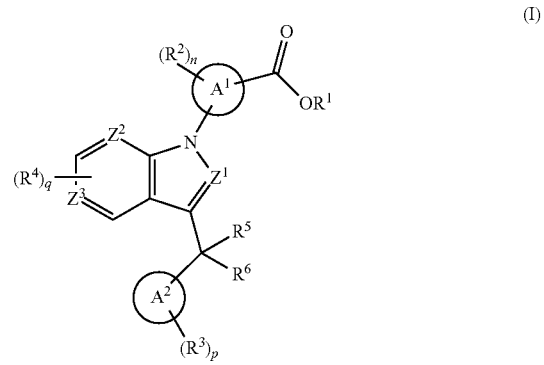

wherein $Z^1$ is $CR^7$ or N;
each $R^7$ is independently H, $C_{1-4}$ alkyl; $C_{1-4}$ haloalkyl, halo, CN, $NO_2$;
$Z^2$ and $Z^3$ are each independently $CR^{10}$ or N;
each $R^{10}$ is independently H, $R^{15}$ or $C_{1-4}$ alkyl optionally substituted with one or more $R^{15}$;
  where each $R^{15}$ is independently halo, CN, $NO_2$, $OR^{16}$, $C(O)R^{16}$, $C(O)OR^{16}$, $C(O)NR^{16}R^{17}$, $SR^{16}$, $SOR^{16}$, $SO_2R^{16}$, $NR^{16}R^{17}$ or $NR^{18}C(O)R^{16}$;
    where each $R^{16}$ and $R^{17}$ is independently hydrogen, $C_{1-6}$ alkyl optionally substituted with one or more halo substituents, $C_{3-8}$ cycloalkyl, optionally substituted with one or more halo substituents or $C_{5-7}$ heterocyclyl optionally substituted with one or more halo substituents; and $R^{18}$ is H or $C_{1-4}$ alkyl;
$A^1$ is phenyl or a 5- or 6-membered heteroaryl ring;
$R^1$ is H or $C_{1-6}$ alkyl optionally substituted with one or more substituents selected from halo, OH or phenyl, wherein phenyl groups may optionally substituted with 1 to 3 substituents selected from OH, CN, $NO_2$, halo, $C_{1-4}$ alkyl and $C_{1-4}$ haloalkyl;
each $R^2$ is independently halo, CN, $NO_2$, $OR^{11}$ or $NR^{11}R^{12}$;
  where each $R^{11}$ and $R^{12}$ is independently hydrogen, $C_{1-4}$ alkyl optionally substituted with one or more halo substituents, or $C_{3-8}$ cycloalkyl, optionally substituted with one or more halo substituents; or
  $R^2$ may also be $C_{1-6}$ alkyl optionally substituted with one or more substituents selected from phenyl, halo, CN, $NO_2OR^{11}$, $NR^{11}R^{12}$, where each $R^{11}$ and $R^{12}$ is as defined above;
n is 0 to 4 where $A^1$ is a 6-membered ring or 0 to 3 where $A^1$ is a 5-membered ring;
$A^2$ is phenyl or pyridyl;
each $R^3$ is independently halo, CN, $NO_2OH$, $OR^{13}$ or $NR^{13}R^{14}$;
  where each $R^{13}$ and $R^{14}$ is independently hydrogen, $C_{1-4}$ alkyl, $C_{3-8}$ cycloalkyl or $C_{5-7}$ heterocyclyl, any of which may optionally be substituted with one or more substituents selected from halo, $C_{1-4}$ alkoxy or oxo or $R^{13}$ and $R^{14}$ together with the nitrogen atom to which they are attached may form a 4-7 membered heterocyclic ring optionally containing one or more further heteroatoms selected from N, O and S and optionally substituted with one or more substituents selected from halo, $C_{1-4}$ alkoxy and oxo;

or $R^3$ may also be $C_{1-8}$ alkyl, $C_{2-8}$ alkenyl, $C_{3-8}$ cycloalkyl or $C_{5-7}$ heterocyclyl, any of which is optionally substituted with one or more substituents selected from phenyl, halo, CN, $NO_2OH$, $OR^{13}$, $NR^{13}R^{14}$, where each $R^{13}$ and $R^{14}$ is as defined above;

p is 0 to 5;

each $R^4$ is independently $R^{15}$ or $C_{1-4}$ alkyl optionally substituted with one or more $R^{15}$;

where $R^{15}$ is as defined above;

q is 0 to 2;

each of $R^5$ and $R^6$ is H or when:
$A^1$ is other than phenyl; or
$A^2$ is other than phenyl; or
$R^3$ is other than halogen, $C_{1-8}$ alkyl optionally substituted with halo or $C_{3-8}$ cycloalkyl; or
$R^2$ is other than halo or OH;
$R^5$ and $R^6$ together may form =O;

or a pharmaceutically or veterinarily acceptable salt, solvate or hydrate thereof or a deuterated or tritiated variant thereof, including all stereoisomers.

The compounds of the invention are inhibitors of RORγt and are therefore of use in the treatment and prevention of a number of inflammatory and autoimmune conditions.

WO 2004/020409 and WO 2009/005672 both relate to compounds which are somewhat similar to the compounds of general formula (I) but which are PPARγ agonists rather than RORγt inhibitors. WO 2015/087234 relates to RORγt inhibitors of similar structure to the compounds of general formula (I).

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification the term "$C_{1-6}$ alkyl" refers to a fully saturated straight or branched hydrocarbon chain having from 1 to 6 carbon atoms. Examples include methyl, ethyl, n-propyl, isopropyl, t-butyl, n-hexyl.

The term "$C_{1-4}$ alkyl" has a similar meaning but refers to alkyl groups with between 1 and 4 carbon atoms.

The term "$C_{3-8}$ cycloalkyl" refers to a fully saturated hydrocarbon ring having from 3 to 8 carbon atoms. Examples include cyclopropyl, cyclopentyl and cyclohexyl.

The term "$C_{1-6}$ haloalkyl" refers to a $C_{1-6}$ alkyl group as defined above in which one or more hydrogen atoms are replaced by halo atoms. Haloalkyl groups may have any number of halo substituents from 1 to perhalosubstituted. Examples include chloromethyl, trifluoromethyl, 1-bromoethyl, 1,1,2,2-tetrafluoroethyl etc.

The term "$C_{6-7}$ heterocyclyl" refers to a non-aromatic ring having from 5 to 7 carbon atoms and at least one ring heteroatom selected from N, O and S. Examples include tetrahydrofuranyl, piperidinyl, morpholinyl and piperazinyl.

In the present specification, "halo" refers to fluoro, chloro, bromo or iodo.

The term "aryl" in the context of the present specification refer to a ring system with aromatic character having from 5 to 14 ring carbon atoms unless specified otherwise, and containing up to three rings. Where an aryl group contains more than one ring, not all rings must be fully aromatic in character. Examples of aromatic moieties are benzene, naphthalene, indane and indene.

The term "heteroaryl" in the context of the specification refer to a ring system with aromatic character having from 5 to 14 ring atoms (unless specified otherwise) at least one of which is a heteroatom selected from N, O and S, and containing up to three rings. Where a heteroaryl group contains more than one ring, not all rings must be fully aromatic in character. Examples of heteroaryl groups include pyridine, pyrimidine, indole, benzofuran, benzimidazole and indolene.

The term "oxo" refers to a C=O group. The carbon atom may be part of an alkyl chain or a cycloalkyl or heterocyclyl ring.

The terms "deuterated variant" and "tritiated variant" refer respectively to compounds in which one or more of the hydrogen atoms is a deuterium atom or is a tritium atom.

Appropriate pharmaceutically and veterinarily acceptable salts of the compounds of general formulae (I) include basic addition salts such as sodium, potassium, calcium, aluminium, zinc, magnesium and other metal salts as well as choline, diethanolamine, ethanolamine, ethyl diamine, megulmine and other well-known basic addition salts as summarised in Paulekuhn et al., (2007) *J. Med. Chem.* 50: 6665-6672 and/or known to those skilled in the art.

Salts which are not pharmaceutically or veterinarily acceptable may still be valuable as intermediates.

In some suitable compounds of the present invention the group $A^1$ is phenyl or a 5- or 6-membered heteroaryl ring selected from phenyl, pyridyl, pyridazinyl, pyrazinyl, pyrimidinyl, pyrrolyl, pyrazolyl, imidazolyl or furanyl.

More suitably, however, the group $A^1$ is phenyl or a 6-membered aryl group, for example phenyl, pyridyl or pyrimidinyl.

In some particularly suitable compounds, $A^1$ is phenyl and in other particularly suitable compounds, $A^1$ is pyridyl.

When the group $A^1$ is a 6-membered ring (including phenyl and pyridyl) the group $C(O)OR^1$ may be positioned at the meta or para position of the ring relative to the remainder of the molecule. For example when $A^1$ is phenyl, the group $C(O)OR^1$ is suitably at the 3- or 4-position of the ring.

In particularly suitable compounds, the group $C(O)OR^1$ is positioned at the para position of the ring relative to the remainder of the molecule. For example when $A^1$ is phenyl, the group $C(O)OR^1$ is most suitably at the 4-position of the ring.

When $A^1$ is pyridyl, it is suitably a 2-pyridyl group (i.e. the nitrogen atom is adjacent the atom which links $A^1$ to the remainder of the molecule) or a 3-pyridyl group. As discussed above, the $C(O)OR^1$ group is suitably at the para position with respect to the remainder of the molecule. Thus, when $A^1$ is a 2-pyridyl group, the $C(O)OR^1$ group may be at the 5-position of the pyridine ring and when $A^1$ is a 3-pyridyl group, the $C(O)OR^1$ group may be at the 6-position of the pyridine ring.

In some suitable compounds of the present invention, $A^2$ is phenyl. In other suitable compounds of the present invention, $A^2$ is pyridyl, particularly 4-pyridyl.

Some particularly suitable compounds of the present invention are compounds of general formula (IA), in which both $A^1$ and $A^2$ are phenyl:

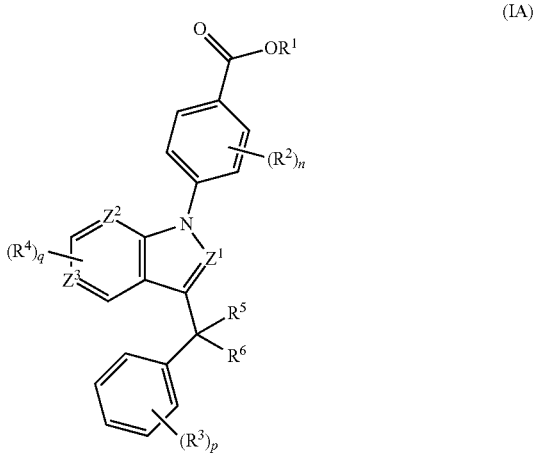

wherein $R^1$, $R^2$, $R^3$, $R^4$, $R^5$, $R^6$, $Z^1$, $Z^2$, $Z^3$, n, p and q are as defined above.

In some suitable compounds of general formulae (I) and (IA), the group $R^1$ may be H, $C_{1-6}$ alkyl or benzyl and in particularly suitable compounds, $R^1$ is H.

Suitably, in compounds of general formulae (I) and (IA), n is 0 to 2 and $R^2$, when present is chloro, fluoro, methyl or trifluoromethyl. In some particularly suitable compounds of this type, n is 1 and $R^2$ is chloro or fluoro, especially fluoro. Suitably, in this case the chloro or fluoro group is positioned at the 2-position of the $A^1$ ring, i.e. the position adjacent the atom via which the phenyl ring is linked to the remainder of the molecule.

Alternatively, in compounds of general formulae (I) and (IA), n is 0 to 2 and $R^2$, when present is OH. In such compounds, n may be 0 or 1 and the OH group, when present may be at the 3-position of the $A^1$ ring, with the $C(O)OR^1$ group at the 4-position of the ring with respect to the remainder of the molecule.

More suitably, n is 0 or 1.

In some suitable compounds general formulae (I) and (IA), each $R^3$ is independently halo, CN, $NO_2OH$, $NR^{12}R^{13}$;
where each $R^{12}$ and $R^{13}$ is independently hydrogen, $C_{1-2}$ alkyl optionally substituted with one or more halo substituents, or $C_{3-7}$ cycloalkyl, optionally substituted with one or more halo substituents;
or $R^3$ may also be $C_{1-4}$ alkyl optionally substituted with one or more substituents selected from phenyl, halo, CN, $NO_2OH$, $NR^{12}R^{13}$, where each $R^{12}$ and $R^{13}$ is as defined above.

More suitably, each $R^3$ is independently fluoro, chloro, bromo, CN, $NO_2$, OH, $NH_2$, $NHCH_3$, $N(CH_3)_2$, $C_{1-4}$ alkyl or $C_{1-4}$ alkyl substituted with one or more halo substituents.

In some particularly suitable compounds general formulae (I) and (IA), each $R^3$ is independently halo or $C_{1-4}$ haloalkyl, for example chloro, fluoro, bromo or trifluoromethyl and p is suitably 0-3, for example 1 or 2 and especially 2.

When p is 2, one of the $R^3$ groups may be halo and the other may be trifluoromethyl.

Particularly suitable compounds of the present invention include compounds of formula (IA) in which p is 2 and the substituents $R^3$ are positioned at the 2- and 6-positions of the phenyl ring. Especially suitable compounds of this type are those in which one $R^3$ group is halo, especially chloro, fluoro or bromo, more especially chloro or fluoro, and the other is $C_{1-4}$ halo alkyl, especially trifluoromethyl.

Other particularly suitable compounds of the present invention include compounds of general formula (I) wherein $A^1$ is phenyl and $A^2$ is 4-pyridyl, p is 2 and the substituents $R^3$ are positioned at the 2- and 6-positions of the phenyl ring. Especially suitable compounds of this type are those in which one $R^3$ group is halo, especially chloro, fluoro or bromo, more especially chloro or fluoro, and the other is $C_{1-4}$ halo alkyl, especially trifluoromethyl.

Other particularly suitable compounds of the present invention include compounds of general formula (I) wherein $A^1$ is a 2-pyridyl group wherein the $C(O)OR^1$ group is at the 5-position of the pyridine ring or $A^1$ is a 3-pyridyl group, wherein the $C(O)OR^1$ group is at the 6-position of the pyridine ring; and wherein $A^2$ is phenyl, p is 2 and the substituents $R^3$ are positioned at the 2- and 6-positions of the phenyl ring. Especially suitable compounds of this type are those in which one $R^3$ group is halo, especially chloro, fluoro or bromo, more especially chloro or fluoro, and the other is $C_{1-4}$ halo alkyl, especially trifluoromethyl.

In compounds of general formulae (I) and (IA), $R^4$, where present is suitably halo, $C_{1-4}$ alkyl or $C_{1-4}$ haloalkyl, for example chloro, fluoro, methyl or trifluoromethyl. In some more suitable compounds $R^4$ is methyl, chloro or fluoro and q is 1.

In other suitable compound of the present invention, q is 0 and so $R^4$ is not present.

In some suitable compounds of the present invention, $Z^1$ is $CR^7$.

In other compounds of the present invention $Z^3$ is $CR^{10}$.

In further compounds of the present invention, $Z^2$ is $CR^{10}$.

In further suitable compounds of the present invention, $Z^1$ is is $CR^7$ and $Z^3$ is $CR^{10}$.

In still other compounds of the present invention $Z^1$ is $CR^7$ and $Z^2$ and $Z^3$ are both $CR^{10}$.

In further suitable compounds of the present invention, both $Z^2$ and $Z^3$ are $CR^{10}$ and $Z^1$ is N.

In other compounds $Z^1$ is $CR^7$ and $Z^2$ and $Z^3$ are both N.

In other compounds $Z^1$ is is $CR^7$, $Z^3$ is $CR^{10}$ and $Z^2$ is N.

In all such compounds, $R^7$ and $R^{12}$ are as defined above for general formula (I) but are more suitably H or $C_{1-4}$ alkyl, especially H or methyl and particularly H.

Examples of compounds of the present invention include:
4-(3-{[2-chloro-6-(trifluoromethyl)phenyl]methyl}-1H-pyrrolo[2,3-b]pyridin-1-yl)benzoic acid (Compound 1)
4-(3-{[2-chloro-6-(trifluoromethyl)phenyl]methyl}-1H-indol-1-yl)benzoic acid (Compound 2)
4-[5-[2-chloro-6-(trifluoromethyl)benzoyl]pyrrolo[2,3-d]pyrimidin-7-yl]benzoic acid (Compound 3)
4-[3-(2-fluoro-6-methoxy-benzoyl)indol-1-yl]benzoic acid (Compound 4)
4-[7-fluoro-3-(2-fluoro-6-methoxy-benzoyl)indol-1-yl]benzoic acid (Compound 5)
4-[3-[[2-chloro-6-(trifluoromethyl)phenyl]methyl]indol-1-yl]-2-hydroxy-benzoic acid (Compound 6)
4-[3-[2-chloro-6-(trifluoromethyl)benzoyl]-7-methyl-indol-1-yl]benzoic acid (Compound 7)
6-[3-[2-chloro-6-(trifluoromethyl)benzoyl]-7-fluoro-indol-1-yl]pyridine-3-carboxylic acid (Compound 8)
4-[3-(2,6-dichlorobenzoyl)-7-methyl-indol-1-yl]benzoic acid (Compound 9)
4-[3-(2-fluoro-6-methoxy-benzoyl)indazol-1-yl]benzoic acid (Compound 10)
4-[3-[2-fluoro-6-(trifluoromethyl)benzoyl]-7-methyl-indol-1-yl]benzoic acid (Compound 11)
4-[7-fluoro-3-[2-fluoro-6-(trifluoromethoxy)benzoyl]indol-1-yl]benzoic acid (Compound 12)

3-fluoro-4-[7-fluoro-3-[2-fluoro-6-(trifluoromethoxy)benzoyl]indol-1-yl]benzoic acid (Compound 13)
4-[3-[2-fluoro-6-(trifluoromethoxy)benzoyl]indol-1-yl]benzoic acid (Compound 14);
5-[3-(2,6-dichlorobenzoyl)indazol-1-yl]pyridine-2-carboxylic acid (Compound 15);
6-[3-(2,6-dichlorobenzoyl)indazol-1-yl]pyridine-3-carboxylic acid (Compound 16);
6-[3-[(2,6-dichlorophenyl)methyl]indazol-1-yl]pyridine-3-carboxylic acid (Compound 17);
4-[3-[[2-chloro-6-(trifluoromethyl)phenyl]methyl] indazol-1-yl]benzoic acid (Compound 18);
6-[3-[[2-chloro-6-(trifluoromethyl)phenyl]methyl]indol-1-yl]pyridine-3-carboxylic acid (Compound 19);
6-[3-[[2-chloro-6-(trifluoromethyl)phenyl]methyl]-7-fluoro-indol-1-yl]pyridine-3-carboxylic acid (Compound 20);
5-[3-[2-chloro-6-(trifluoromethyl)benzoyl]indol-1-yl]pyridine-2-carboxylic acid (Compound 21);
6-[3-[2-chloro-6-(trifluoromethyl)benzoyl]indol-1-yl]pyridine-3-carboxylic acid (Compound 22);
6-[3-[2-chloro-6-(trifluoromethyl)benzoyl]pyrrolo[2,3-b]pyridin-1-yl]pyridine-3-carboxylic acid (Compound 23);
5-[3-[2-chloro-6-(trifluoromethyl)benzoyl]pyrrolo[2,3-b]pyridin-1-yl]pyridine-2-carboxylic acid (Compound 24);
5-[3-[2-chloro-6-(trifluoromethyl)benzoyl]indazol-1-yl]pyridine-2-carboxylic acid (Compound 25);
6-[3-[2-chloro-6-(trifluoromethyl)benzoyl]indazol-1-yl]pyridine-3-carboxylic acid (Compound 26);
4-[3-[[2-chloro-6-(trifluoromethyl)phenyl]methyl]-7-fluoro-indol-1-yl]benzoic acid (Compound 27);
sodium 4-{3-[3-chloro-5-(trifluoromethyl)pyridine-4-carbonyl]indol-1-yl}benzoate (Compound 28);
sodium 4-(3-{[3-chloro-5-(trifluoromethyl)pyridin-4-yl]methyl}indol-1-yl)benzoate (Compound 29);
6-(3-{[2-chloro-6-(trifluoromethyl)phenyl]methyl}indazol-1-yl)pyridine-3-carboxylic acid (Compound 30);
4-(3-{[2-chloro-6-(trifluoromethyl)phenyl]methyl}pyrrolo[3,2-c]pyridin-1-yl)benzoic acid (Compound 31);
6-{3-[2-chloro-6-(trifluoromethyl)benzoyl]pyrazolo[3,4-b]pyridin-1-yl}pyridine-3-carboxylic acid (Compound 32);
5-(3-{[2-chloro-6-(trifluoromethyl)phenyl]methyl}indazol-1-yl)pyridine-2-carboxylic acid (Compound 33);
4-{3-[2-chloro-6-(trifluoromethyl)benzoyl]pyrrolo[3,2-c]pyridin-1-yl}benzoic acid (Compound 34);
6-{3-[2-chloro-6-(trifluoromethyl)benzoyl]-7-fluoroindazol-1-yl}pyridine-3-carboxylic acid (Compound 35);
4-(3-{[2-chloro-6-(trifluoromethyl)phenyl]methyl}-7-fluoroindol-1-yl)-2-hydroxybenzoic acid (Compound 36);
$C_{1-6}$ alkyl and benzyl esters thereof; and, their pharmaceutically or veterinarily acceptable salts or free acids, solvates or hydrates or a deuterated or tritiated variant thereof, including all stereoisomers.

Compounds of general formula (I) in which $R^1$ is hydrogen may be prepared from compounds of general formula (I) in which $R^1$ is other than hydrogen by hydrolysis with an acid or a base. More suitably base hydrolysis is used in which the compound of formula (I) in which $R^1$ is other than H is reacted with a strong base such as sodium or potassium hydroxide. Typically, the reaction is carried out in a polar organic solvent such as dioxane or in an alcoholic solvent and at a temperature of about 15 to 55° C. In some cases the hydrolysis may be conducted at 15 to 25° C., for example at room temperature but in other cases a higher temperature may be more suitable, for example 40-50° C.

Compounds of general formula (I) in which $R^1$ is other than hydrogen may be prepared from compounds of general formula (II):

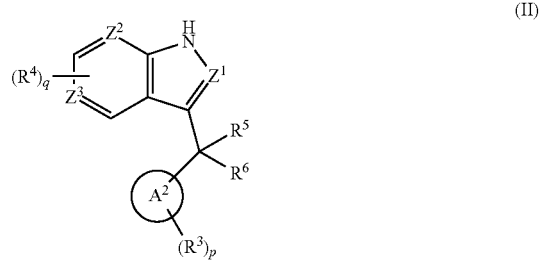

(II)

wherein $A^2$, $Z^1$, $Z^2$, $Z^3$, $R^3$, $R^4$, $R^5$, $R^6$, p and q are as defined in general formula (I); by reaction with a compound of general formula (III):

(III)

wherein $R^1$ is $C_{1-6}$ alkyl optionally substituted with one or more substituents selected from halo, OH or phenyl, wherein phenyl groups may optionally substituted with 1 to 3 substituents selected from OH, CN, $NO_2$, halo, $C_{1-4}$ alkyl and $C_{1-4}$ haloalkyl; and $A^1$, $R^2$ and n are as defined for general formula (I); and $X^1$ is a leaving group, such as a halogen, typically iodine or bromine.

The coupling of compounds of general formulae (II) and (III) may be carried out using an Ullman reaction using a copper (I) salt, for example copper (I) iodide in the presence of a weak base, such as potassium carbonate or caesium carbonate and if necessary using a catalyst such as (L)-proline.

Compounds of general formula (III) are well known and are readily available or may be prepared by methods well known to those of skill in the art.

Compounds of general formula (II) are new and themselves form a further aspect of the invention.

Compounds of general formula (II) may be prepared from compounds of general formula (IV):

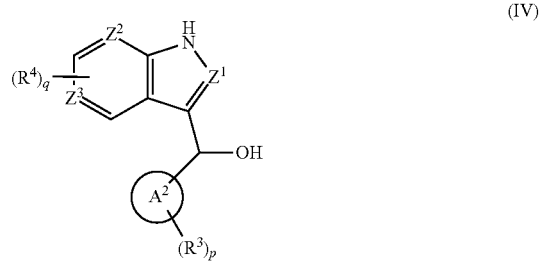

(IV)

wherein $A^2$, $Z^1$, $Z^2$, $Z^3$, $R^3$, $R^4$, p and q are as defined in general formula (I).

Compounds of general formula (II) in which $R^5$ and $R^6$ together form ↑O may be prepared by oxidation of a compound of general formula (IV), typically using Dess-Martin periodinane. The reaction may be carried out in a polar organic solvent such as tetrahydrofuran and at a temperature of −5 to 5° C., typically at about 0° C.

Compounds of general formula (II) in which $R^5$ and $R^6$ are both hydrogen may be prepared by reduction of a compound of general formula (IV), for example using a silane reducing agent such as triethylsilane in the presence of an acid, typically trifluoroacetic acid. An alternative reduction method is the use of a reducing agent such as hypophosphorous acid. Suitably, the compound of formula (IV) is reacted with hypophosphorous acid in the presence of iodine and the reaction may be conducted in a solvent such as acetic acid and at elevated temperature, for example 120 to 180° C. and with microwave radiation.

Compounds of general formula (II) in which $R^5$ and $R^6$ are both hydrogen may also be prepared by reduction of a compound of general formula (IVa):

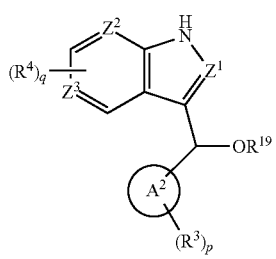

(IVa)

wherein $A^2$, $Z^1$, $Z^2$, $Z^3$, $R^3$, $R^4$, p and q are as defined in general formula (I) and $R^{19}$ is $C_{1-6}$ alkyl under the same conditions as the reduction of compounds of general formula (IV).

Compounds of general formula (IV) in which $Z^1$ is $CR^7$ may be prepared by the reaction of a compound of general formula (V):

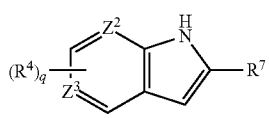

(V)

wherein $Z^2$, $Z^3$, $R^4$, $R^7$ and q are as defined for general formula (I); with a compound of general formula (VI):

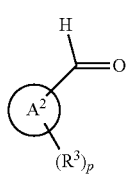

(VI)

wherein $A^2$, $R^3$ and p are as defined for general formula (I).

The reaction may be carried out under basic conditions, for example in the presence of sodium or potassium hydroxide and in an alcoholic solvent such as methanol or ethanol.

Compounds of general formula (IVa) are a byproduct of the reaction between the compounds of general formulae (V) and (VI).

Compounds of general formulae (V) and (VI) are known and are readily available or may be prepared by methods well known to those of skill in the art.

Compounds of general formula (IV) in which $Z^1$ is N may be prepared by the reaction of a compound of general formula (VII):

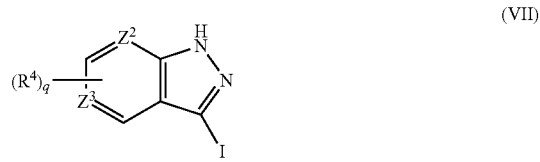

(VII)

wherein $Z^2$, $Z^3$, $R^4$ and q are as defined for general formula (I); by reaction with a Grignard reagent, for example an alkyl or aryl magnesium bromide, followed by reaction with a compound of general formula (VI) as defined above in the presence of a complex such as bromo(2-methylphenyl) magnesium and isopropyl magnesium chloride. lithium chloride.

The reaction may be carried out at reduced temperature, typically −15 to 0° C., more usually −10 to −5° C. in an organic solvent such as diethyl ether.

A compound of general formula (VII) may be prepared from a compound of general formula (VIII):

(VIII)

wherein $Z^2$, $Z^3$, $R^4$ and q are as defined for general formula (I); by reaction with iodine under basic conditions, for example in the presence of sodium or potassium hydroxide and in an organic solvent such as N,N'-dimethylformamide.

Compounds of general formula (VIII) are known and are readily available or may be synthesised by methods well known to those of skill in the art.

An alternative method for the preparation of a compound of general formula (I) in which $R^5$ and $R^6$ together form a carbonyl group is by the reaction of a compound of general formula (IX):

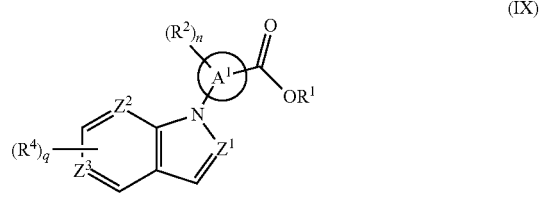

(IX)

wherein $A^1$, $Z^1$, $Z^2$, $Z^3$, $R^1$, $R^2$, $R^4$, n and q are as defined in general formula (I) with a compound of general formula (X):

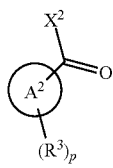
(XI)

wherein $A^2$, $R^3$ and p are as defined for general formula (I) and $X^2$ is a leaving group, such as a halo group, typically chloro.

The reaction may be carried out under basic conditions, for example in the presence of an organometallic agent such as dimethylaluminium chloride and in an organic solvent such as dichloromethane. Typically the reaction takes place at ambient temperature, usually 15-25° C. Usually, the product of general formula (I) is a compound in which $R^1$ is hydrogen.

Compounds of general formulae (X) and (XI) are known and are readily available or may be prepared by a person of skill in the art using known methods.

The compounds of the present invention are useful in the treatment of diseases and conditions mediated by RORγt, in particular inflammatory and autoimmune diseases.

Therefore, in a further aspect of the invention, there is provided a compound of general formula (I) or (IA) as defined above for use in medicine, particularly for use in the treatment or prevention of diseases and conditions mediated by RORγt, in particular inflammatory and autoimmune diseases.

More specifically, there is provided a compound of general formula (I) or (IA) as defined above for use in the treatment or prevention of asthma, chronic obstructive pulmonary disease (COPD), bronchitis, allergic diseases, such as allergic rhinitis and atopic dermatitis, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease or scleritis.

In a further aspect, there is provided the use of a compound of general formula (I) or (IA) in the preparation of an agent for the treatment or prevention of asthma, chronic obstructive pulmonary disease (COPD), bronchitis, allergic diseases, such as allergic rhinitis and atopic dermatitis, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease or scleritis.

In addition, the invention provides a method for the treatment of a disease or condition selected from the group consisting of asthma, chronic obstructive pulmonary disease (COPD), bronchitis, allergic diseases, such as allergic rhinitis and atopic dermatitis, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease or scleritis, the method comprising administering to a patient in need of such treatment and effective amount of a compound of general formula (I) or (IA).

The compounds of the present invention will generally be administered to a patient in a suitable pharmaceutical formulation. Therefore, in a further aspect of the invention there is provided a pharmaceutical or veterinary composition comprising a compound of general formula (I) or (IA) together with a pharmaceutically or veterinarily acceptable excipient or carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) or (II) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) or (IA) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg; so as to maintain the concentration of drug in the plasma at a concentration effective to inhibit RORγt.

Compounds of general formula (I) or (IA) may be used in combination with one or more other active agents which are useful in the treatment of the diseases and conditions listed above. These active agents may be other RORγt inhibitors but will more usually have a different mechanism of action.

Therefore the pharmaceutical composition may also contain one or more of such additional active agents.

There is also provided a combined preparation comprising a compound of formula (I) or (IA) together with an additional active ingredient, for simultaneous, sequential or separate use in the treatment of a disease or condition mediated by RORγt as described above.

The invention will now be described in greater detail with reference to the following non-limiting examples. In the examples, the following abbreviations are used.

| DCM | Dichloromethane |
| DMSO | Dimethylsulfoxide |
| EtOAc | Ethyl acetate |
| FCC | Flash column chromatography |
| LCMS | Liquid chromatography-mass spectrometry |
| MeCN | Acetonitrile |
| rt | Room temperature |
| THF | Tetrahydrofuran |
| tr | Retention time |

GENERAL EXPERIMENTAL DETAILS

Examples 1 and 2 and Compounds 19-36

Commercially available reagents and solvents (HPLC grade) were used without further purification. $^1$H NMR spectra were recorded on a Bruker DRX 500 MHz spectrometer or a Bruker DPX 250 MHz spectrometer in deuterated solvents.

Chemical Shifts (δ) are in Parts Per Million.

Analytical HPLC-MS (METCR1673), was performed on Shimadzu LCMS-2010EV systems using reverse phase Supelco Ascentis Express (2.7 μm, 2.1×30 mm), gradient 5-100% B (A=water/0.1% formic acid, B=acetonitrile/0.1% formic acid) over 1.6 minutes injection volume 3 μL, flow=1.0 mL/minute. UV spectra were recorded at 215 nm using a SPD-M20A photo diode array detector. Mass spectra were obtained over the range m/z 100 to 100 at a sampling rate of 2 scans per second using a LCMS2010EV. Data were integrated and reported using Shimadzu LCMS-Solutions andPsiPort software.

Alternatively, (MET-uHPLC-AB-101) analytical HPLC-MS were performed on a Waters Acquity UPLC system with Waters PDA and ELS detectors using a PhenomenexKinetex-XB C-18 column, (1.7 μM, 2.1 mm×100 mm at a column temperature of 40° C., gradient 5-100% B (A=water/0.1% formic acid; B=acetonitrile/0.1% formic acid) over 5.3 minutes, then 100% B for 0.5 minute, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynxsoftware.

Examples 3-9

Reverse phase HPLC was performed with a Waters FractionLynx system with integrated MS detection. Chromatographic conditions; Gradient 5-95% ACN in 0.1 M HCO2H, pH3. Column: Waters Sunfire C18 ODB 5μ 19×150 mm.

Reverse phase HPLC on SCF was performed with a Waters Prep100 SCF system with integrated MS detection. Chromatographic conditions; MeOH/NH3 20 mM, Column: Phenomenex Luna Hilic 5μ, 30×250 mm.

Analytical LC-MS experiments were performed using a Waters Acquity system combined with a Waters Xevo Q-ToF Mass or a Shimadzu 2010EV UPLC system in ESI mode. Chromatographic conditions: gradient 5-90% ACN, pH10. Column: Waters Acquity BEH C18 1.7μ 2.1×50 mm.

NMR spectra were recorded on a Bruker Avance, Avance II or Avance III spectrometer at a proton frequency of 300, 400, 500 or 600 MHz. The central peaks of chloroform-δ (H 7.26 ppm), CD3OD (H 3.30 ppm) or DMSO-d6 (H 2.49 ppm) were used as internal references.

Unless otherwise stated, starting materials were commercially available or previously described in the literature. All Example 1—Synthesis of sodium 4-(3-{[2-chloro-6-(trifluoromethyl)phenyl] methyl}-1H-pyrrolo[2,3-b]pyridin-1-yl)benzoate (Compound 1 sodium salt)

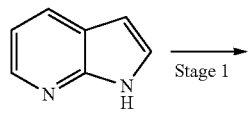
Stage 1

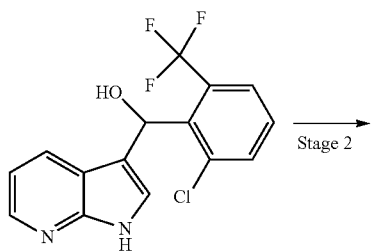
Stage 2

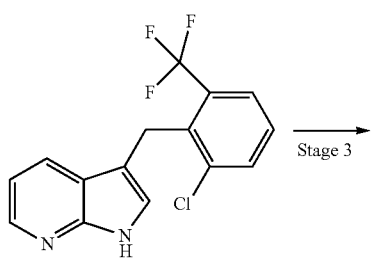
Stage 3

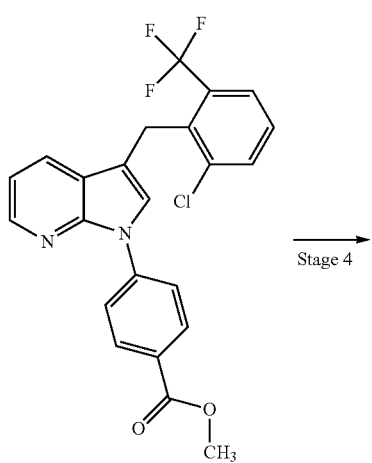
Stage 4

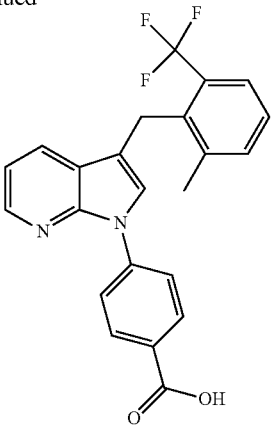

Stage 1: Synthesis of [2-chloro-6-(trifluoromethyl)phenyl](1H-pyrrolor2,3-blpyridin-3-yl]methanol 2-chloro-6-(trifluoromethyl)benzaldehyde (5.3 g, 25.39 mmol) was added to a solution of 1H-pyrrolo[2,3-b]pyridine (3 g, 25.39 mmol) in methanol (125 mL) and stirred at rt followed by the addition of a solution of potassium hydroxide (4.27 g, 76.18 mmol) in methanol (125 mL). The reaction was stirred at rt for 3 nights then concentrated to afford an orange oil which was partitioned between water (100 mL) and EtOAc (100 mL). The aqueous layer was extracted with EtOAc (2×40 mL), combined and washed with water (3×50 mL), brine (5 mL), dried using $MgSO_4$, filtered and evaporated to dryness to afford 8 g of colourless oil. The crude material was purified by FCC eluting in a gradient of 0-100% EtOAc in heptanes to afford 3.47 g (40% yield) desired product [2-chloro-6-(trifluoromethyl)phenyl](1H-pyrrolo[2,3-b]pyridin-3-yl)methanol as a white solid. 1H NMR (500 MHz, Chloroform-d) δ9.21 (s, 1H), 8.31 (dd, J=4.8, 1.5 Hz, 1H), 7.90 (dd, J=7.9, 1.4 Hz, 1H), 7.74 (d, J=7.3 Hz, 1H), 7.63 (d, J=8.0 Hz, 1H), 7.45 (t, J=8.0 Hz, 1H), 7.06 (dd, J=7.9, 4.8 Hz, 1H), 6.86 (dd, J=2.2, 1.4 Hz, 1H), 6.62 (d, J=4.9 Hz, 1H), 3.51 (s, 1H). LC/MS (METCR1673 Generic 2 minutes) tr=1.05 min, 100% m/z=327/329 [M+H]

Also isolated from the FCC was 3.05 g of orange oil which was a mixture of 3-{[2-chloro-6-(trifluoromethyl)phenyl](methoxy)methyl}-1H-pyrrolo[2,3-b]pyridine (65% UV) and hydroxy [2-chloro-6-(trifluoromethyl)phenyl](1H-pyrrolo[2,3-b]pyridin-3-yl)methanol (35% UV).

Stage 2: Synthesis of 3-{[2-chloro-6-(trifluoromethyl)phenyl]methyl}-1H-pyrrolo[2,3-b]pyridine A solution of [2-chloro-6-(trifluoromethyl)phenyl](1H-pyrrolo[2,3-b]pyridin-3-yl)methanol (400 mg, 1.22 mmol) and triethylsilane (0.39 ml, 2.45 mmol) in DCM (5 mL) was stirred in an ice bath and TFA (0.28 ml, 3.67 mmol) was added dropwise. The reaction was stirred at rt for 72 hours. DCM (10 mL) was added to the reaction followed by water (10 mL). The layers were separated and the organic layer was washed with saturated aqueous sodium bicarbonate solution (2×5 mL), water (5 mL), dried using $MgSO_4$, filtered and evaporated to dryness to afford a yellow solid. The crude material was triturated in DCM and filtered to afford 80 mg (21% yield) of 3-{[2-chloro-6-(trifluoromethyl)phenyl]methyl}-1H-pyrrolo[2,3-b]pyridine as a white solid.

The filtrate was purified by FCC eluting in 0-100% EtOAc in heptane to afford 215 mg (57% yield) as a second batch of 3-{[2-chloro-6-(trifluoromethyl)phenyl]methyl}-1H-pyrrolo[2,3-b]pyridine. 1H NMR (500 MHz, Chloroform-d) δ8.75 (s, 1H), 8.30 (dd, J=4.8, 1.5 Hz, 1H), 7.97-7.92 (m, 1H), 7.67 (d, J=7.9 Hz, 1H), 7.62 (d, J=8.0 Hz, 1H), 7.36 (t, J=8.0 Hz, 1H), 7.10 (dd, J=7.9, 4.8 Hz, 1H), 6.62 (s, 1H), 4.37 (s, 2H). LC/MS (METCR1673 Generic 2 minutes) tr=1.26 min, 98%, m/z=311/313 [M+H]

Stage 3: Synthesis of methyl 4-(3-{[2-chloro-6-(trifluoromethyl)phenyl]methyl}-1H-pyrrolo[2,3-b]pyridin-1-yl)benzoate 3-{[2-chloro-6-(trifluoromethyl)phenyl]methyl}-1H-pyrrolo[2,3-b]pyridine (100 mg, 0.32 mmol), methyl 4-iodobenzoate (93 mg, 0.35 mmol), potassium carbonate (97.86 mg, 0.71 mmol), copper iodide (12.26 mg, 0.064 mmol) and L-proline (14.81 mg, 0.129 mmol) were dissolved in anhydrous DMSO (4 mL) in an Ace pressure tube. The reaction was vigorously degassed with nitrogen for 2 minutes and the resulting blue/green solution was stirred at 100° C. overnight. The reaction was cooled to rt, water (10 mL) was added to the reaction followed by EtOAc (20 mL). The layers were separated and the aqueous layer was extracted with EtOAc (2×20 mL). The combined organic layers were washed with water (4×10 mL), dried using brine (10 mL) and evaporated to dryness to afford a brown solid. The crude material was purified by FCC eluting in a gradient of 0-100% EtOAc in heptanes to afford 70 mg (49% yield) of methyl 4-(3-{[2-chloro-6-(trifluoromethyl)phenyl]methyl}-1H-pyrrolo[2,3-b]pyridin-1-yl)benzoate as a white solid. 1H NMR (500 MHz, Chloroform-d) δ8.41 (dd, J=4.7, 1.5 Hz, 1H), 8.14-8.10 (m, 2H), 7.99 (dd, J=7.9, 1.6 Hz, 1H), 7.84 (d, J=8.8 Hz, 2H), 7.70 (d, J=7.8 Hz, 1H), 7.66 (d, J=8.0 Hz, 1H), 7.40 (t, J=8.0 Hz, 1H), 7.20 (dd, J=7.9, 4.7 Hz, 1H), 6.87 (s, 1H), 4.41 (s, 2H), 3.92 (s, 3H). LC/MS (METCR1673 Generic 2 minutes) tr=1.76 min, 100%, m/z=445/447 [M+H]

Stage 4: Synthesis of Sodium 4-(3-{[2-chloro-6-(trifluoromethyl)phenyl]methyl}-1H-pyrrolo[2,3-b]pyridin-1-yl)benzoate Methyl 4-(3-{[2-chloro-6-(trifluoromethyl)phenyl]methyl}-1H-pyrrolo[2,3-b]pyridin-1-yl)benzoate (0.07 g, 0.16 mmol) was dissolved in dioxane (2 mL). 2 M NaOH (0.16 mL, 0.315 mmol) was added and the solution was stirred at rt for 2 nights. After this time the reaction was filtered to afford a white solid which was washed sequentially with water (2×1 mL) and MeCN (2×1 mL). The resulting white solid was dried until constant weight to afford 45 mg (63% yield) of sodium 4-(3-{[2-chloro-6-(trifluoromethyl)phenyl]methyl}-1H-pyrrolo[2,3-b]pyridin-1-yl)benzoate as a white solid. 1H NMR (500 MHz, DMSO-d6) δ8.34 (dd, J=4.7, 1.5 Hz, 1H), 8.07 (dd, J=7.9, 1.5 Hz, 1H), 7.91 (d, J=8.6 Hz, 2H), 7.85 (dd, J=12.0, 8.0 Hz, 2H), 7.63 (d, J=8.6 Hz, 2H), 7.59 (t, J=8.0 Hz, 1H), 7.22 (dd, J=7.9, 4.7 Hz, 1H), 7.11 (s, 1H), 4.38 (s, 2H). LC/MS (MET-uPLC-AB-101 (7 min, low pH)), tr=4.25 min, 100% m/z=431/433 [M+H].

Example 2—Synthesis of 4-(3-{[2-chloro-6-(trifluoromethyl)phenyl]methyl}-1H-indol-1-yl)benzoic acid (Compound 2)

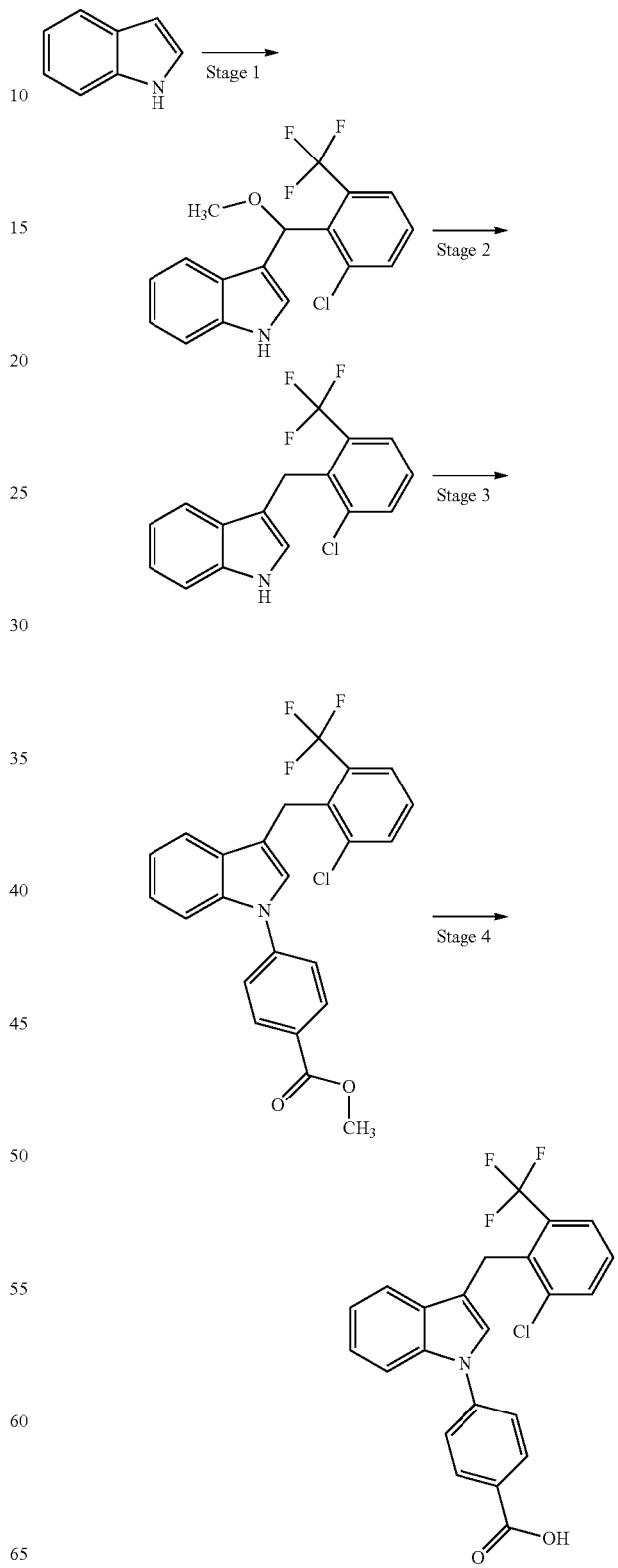

Stage 1: Synthesis of 2-chloro-6-(trifluoromethyl)phenyl](1H-indol-3-yl)methanol and 3-{[2-chloro-6-(trifluoromethyl)phenyl(methoxy)methyl)-1H-indole 2-Chloro-6-(trifluoromethyl)benzaldehyde (890.18 mg, 4.27 mmol) was added to a solution of 1H-indole (500 mg, 4.27 mmol) in methanol (20 mL) followed by the addition of a solution of potassium hydroxide (718.45 mg, 12.8 mmol) in methanol (15 mL). The reaction was stirred at ambient temperature (25-27° C.) overnight. After this time the solvent was reduced in vacuo to approx 5 mL MeOH and the residue partitioned between water (10 mL) and EtOAc (20 mL). The layers were separated and the aqueous layer was extracted with EtOAc (2×20 mL). The combined organic layers were washed with water (2×20 mL), brine (5 mL), dried using MgSO$_4$, filtered and evaporated to dryness to afford 1.5 g orange oil which solidified upon standing to form a solid. The solid was suspended in DCM, filtered and washed with DCM to afford 325 mg white solid. LCMS and NMR analysis confirmed the solid to be a mixture of 3-{[2-chloro-6-(trifluoromethyl)phenyl](methoxy)methyl}-1H-indole (78% UV) and 2-chloro-6-(trifluoromethyl)phenyl](1H-indol-3-yl)methanol (20% UV). The remaining filtrate was evaporated to dryness to afford 800 mg orange gum which was purified by FCC to afford 360 mg (~80% purity, 21% yield) of [2-chloro-6-(trifluoromethyl)phenyl](1H-indol-3-yl)methanol as an orange oil.

3-([2-chloro-6-(trifluoromethyl)phenyl]methoxy)methyl}-1H-indole

1H NMR (500 MHz, DMSO-d6) δ 10.97 (s, 1H), 7.88 (dd, J=8.0, 1.0 Hz, 1H), 7.84 (d, J=8.1 Hz, 1H), 7.64 (t, J=8.0 Hz, 1H), 7.43 (d, J=7.9 Hz, 1H), 7.36 (d, J=8.1 Hz, 1H), 7.12-7.06 (m, 1H), 7.01-6.95 (m, 1H), 6.69 (d, J=1.6 Hz, 1H), 6.15 (s, 1H), 3.35 (s, 3H). LC/MS (METCR1673 Generic 2 minutes) tr=1.51 min, 78%, m/z=309/311 [M+H]

[2-chloro-6-(trifluoromethyl)phenyl](1H-indol-3-yl)methanol

H NMR (500 MHz, Chloroform-d) δ8.05 (s, 1H), 7.71 (dd, J=16.0, 7.7 Hz, 2H), 7.62 (d, J=7.6 Hz, 1H), 7.43 (t, J=8.0 Hz, 1H), 7.38 (d, J=8.2 Hz, 1H), 7.25-7.19 (m, 1H), 7.13 (td, J=7.6, 7.1, 1.0 Hz, 1H), 6.71 (dd, J=2.5, 1.3 Hz, 1H), 6.66 (d, J=10.6 Hz, 1H), 3.42 (d, J=10.5 Hz, 1H). LC/MS (METCR1673 Generic 2 minutes) tr=1.30 min, 91%, m/z=308/310 [M−OH].

Stage 2: Synthesis of 3-{[2-chloro-6-(trifluoromethyl)phenyl]methyl}-1H-indole 3-{[2-chloro-6-(trifluoromethyl)phenyl](methoxy)methyl}-1H-indole (325 mg, 0.96 mmol) and triethylsilane (0.31 ml, 1.91 mmol) were suspended in DCM (3 mL). The reaction was cooled in an ice bath.TFA (0.11 ml, 1.43 mmol) was added dropwise which instantly caused the reaction to go fully into solution. The reaction was stirred at rt for 30 minutes Water (5 mL) was added to the reaction followed by saturated aqueous sodium bicarbonate solution. The layers were separated and the aqueous layer was extracted using DCM (2×5 mL). The combined organic layers were washed with water (2×5 mL), dried using MgSO$_4$, filtered and evaporated to dryness. The residue was dissolved in DCM and re-evaporated ×3 to afford 300 mg pink solid which was triturated in excess heptane with one drop of EtOAc added to afford 170 mg desired product 3-{[2-chloro-6-(trifluoromethyl)phenyl]methyl}-1H-indole as a pink solid. The filtrate was purified by FCC eluting in a gradient of 0-100% EtOAc in heptane to afford an additional 96 mg desired product 3-{[2-chloro-6-(trifluoromethyl)phenyl]methyl}-1H-indole as an orange solid. (266 mg, 90% yield). 1H NMR (500 MHz, Chloroform-d) δ7.88 (s, 1H), 7.67 (dd, J=15.0, 8.1 Hz, 2H), 7.61 (d, J=8.0 Hz, 1H), 7.37-7.33 (m, 2H), 7.22 (td, J=8.1, 7.6, 1.2 Hz, 1H), 7.17 (td, J=7.5, 1.1 Hz, 1H), 6.46-6.43 (m, 1H), 4.39 (s, 2H). LC/MS (METCR1673 Generic 2 minutes) tr=1.56 min, 98%, m/z=310/312 [M+H].

Stage 3: Synthesis of methyl 4-(3-{[2-chloro-6-(trifluoromethyl)phenyl]methyl}-1H-indol-1-yl)benzoate 3-{[2-chloro-6-(trifluoromethyl)phenyl]methyl}-1H-indole (140 mg, 0.45 mmol), methyl 4-iodobenzoate (130.3 mg, 0.5 mmol), potassium carbonate (137.45 mg, 0.99 mmol), copper iodide (17.22 mg, 0.09 mmol) and L-proline (20.79 mg, 0.18 mmol) were dissolved in anhydrous DMSO (4 mL) in an Ace pressure tube. The reaction was vigorously degassed with nitrogen for 2 minutes to give a blue/green solution before stirring at 100° C. overnight. The reaction was cooled to rt, water (10 mL) was added to the reaction followed by EtOAc (20 mL). The layers were separated and the aqueous layer was extracted with EtOAc (2×20 mL). The combined organic layers were washed with water (4×10 mL), and dried using brine (10 mL). The organic layer was dried using MgSO$_4$, filtered and evaporated to dryness to afford −200 mg brown oil. The crude material was purified by FCC eluting in a gradient of 0-100% EtOAc in heptanes to afford 145 mg orange solid. The solid was sonicated in MeCN and the resulting suspension was filtered under vacuum to afford 85 mg (42% yield) of methyl 4-(3-{[2-chloro-6-(trifluoromethyl)phenyl]methyl}-1H-indol-1-yl)benzoate as a white solid. 1H NMR (500 MHz, Chloroform-d) δ8.11 (d, J=8.7 Hz, 2H), 7.74 (dd, J=7.0, 1.4 Hz, 1H), 7.68 (d, J=8.0 Hz, 1H), 7.65-7.60 (m, 2H), 7.47 (d, J=8.7 Hz, 2H), 7.37 (t, J=8.0 Hz, 1H), 7.31-7.28 (part. obsc. m, 2H), 6.61 (s, 1H), 4.43 (s, 2H), 3.93 (s, 3H). LC/MS (METCR1673 Generic 2 minutes) tr=1.84 min, 100%, m/z=444/446 [M+H]

Stage 4: Synthesis of 4-(3-{[2-chloro-6-(trifluoromethyl)phenyl]methyl}-1H-indol-1-yl)benzoic acid 2 M NaOH (0.18 ml, 0.36 mmol) was added to a solution of methyl 4-(3-{[2-chloro-6-(trifluoromethyl)phenyl]methyl}-1H-indol-1-yl)benzoate (80 mg, 0.18 mmol) in dioxane (2 mL) and the solution was stirred at rt for 48 hours. The reaction was evaporated to dryness under a stream of nitrogen. Water (5 mL) was added which formed a thick white suspension. The aqueous was acidified using 2 M HCl and after sonication the reaction remained a thick white suspension. The suspension was filtered under vacuum, washed with excess water and dried until constant weight to afford 70 mg (90% yield) of 4-(3-{[2-chloro-6-(trifluoromethyl)phenyl]methyl}-1H-indol-1-yl)benzoic acid as a white solid. $^1$H NMR (500 MHz, DMSO-d6) δ7.96 (d, J=8.4 Hz, 2H), 7.84 (dd, J=15.8, 8.0 Hz, 2H), 7.71 (d, J=7.8 Hz, 1H), 7.58 (t, J=8.0 Hz, 2H), 7.34 (d, J=8.1 Hz, 2H), 7.24 (t, J=7.3 Hz, 1H), 7.17 (t, J=7.4 Hz, 1H), 6.76 (s, 1H), 4.36 (s, 2H). LC/MS (MET-uPLC-AB-101 (7 min, low pH)), tr=4.57 min, 97% m/z=430/432 [M+H].

Example 3

Synthesis of 4-[3-(2-fluoro-6-methoxy-benzoyl)indol-1-yl]benzoic acid (Compound 4)

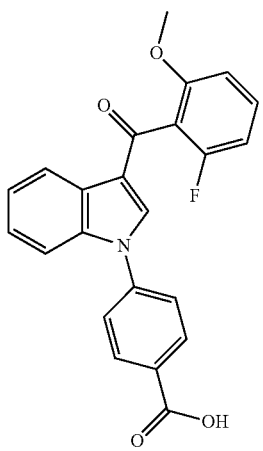 [SMILES: COc1cccc(F)c1C(=O)c1cn(-c2ccc(C(=O)O)cc2)c2ccccc12]

4-(1H-indol-1-yl)benzoic acid (0.025 g, 0.11 mmol) was dissolved in dichloromethane (0.5 mL) and dimethylaluminum chloride (1 M in hexanes) (0.211 mL, 0.21 mmol) was added. 2-fluoro-6-methoxybenzoyl chloride (0.21 mmol), dissolved in dichloromethane (0.5 mL), was added and the resulting mixture was stirred at ambient temperature for 30 mins. The mixture was partitioned between 4 M HCl (2 mL) and dichloromethane (5 mL). The water layer was extracted with dichloromethane (2×5 mL) and the combined organic layer was passed through a phase separator. The organic layer was concentrated under reduced pressure. The residue was dissolved in DMSO (1 mL), filtered and purified by reverse phase HPLC to give the product, yield 75%

$^1$H NMR (600 MHz, DMSO) δ3.76 (s, 3H), 6.93 (t, 1H), 7.02 (d, 1H), 7.37-7.42 (m, 2H), 7.46-7.52 (m, 1H), 7.63-7.66 (m, 1H), 7.74-7.78 (m, 2H), 8.08 (s, 1H), 8.1-8.14 (m, 2H), 8.23-8.28 (m, 1H

Synthesis of 4-[5-[2-chloro-6-(trifluoromethyl)benzoyl]pyrrolo[2,3-d]pyrimidin-7-yl]benzoic acid (Compound 3)

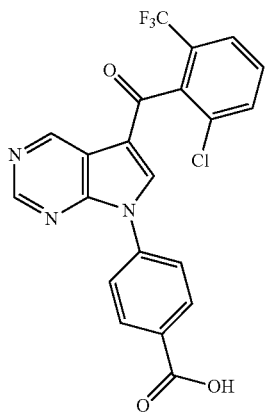 [SMILES: O=C(O)c1ccc(-n2cc(C(=O)c3c(Cl)cccc3C(F)(F)F)c3cncnc32)cc1]

This compound was prepared using a method analogous to that used for Compound 4.

Synthesis of 4-[7-fluoro-3-(2-fluoro-6-methoxy-benzoyl)indol-1-yl]benzoic acid (Compound 5)

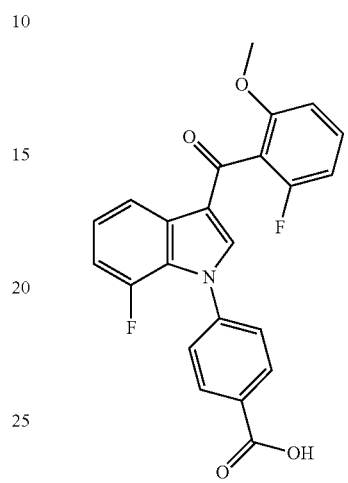

This compound was made using a similar method to that described above for Compound 4, yield 40%.

$^1$H NMR (600 MHz, DMSO) δ3.76 (s, 3H), 6.92 (t, 1H), 7.01 (d, 1H), 7.22 (m, 1H), 7.37 (m, 1H), 7.49 (m, 1H), 7.71 (m, 2H), 8.01-8.07 (m, 3H), 8.10 (d, 1H), 13.25 (s, 1H).

Synthesis of 4-[3-[2-chloro-6-(trifluoromethyl)benzoyl]-7-methyl-indol-1-yl]benzoic acid (Compound 7)

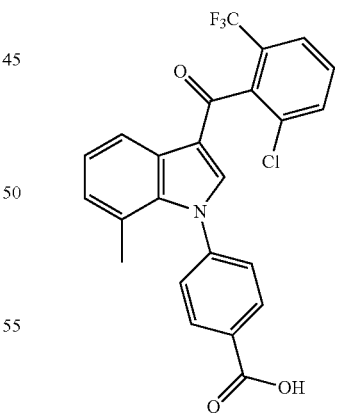

This compound was made using a similar method to that described above for Compound 4, yield 25%.

$^1$H NMR (600 MHz, DMSO) δ1.95 (s, 3H), 7.12 (d, 1H), 7.32 (d, 1H), 7.55-7.62 (m, 2H), 7.72 (d, 1H), 7.81-7.94 (m, 3H), 8.05 (d, 2H), 8.27 (s, 1H).

Expected Number of Hs: 15
Assigned Hs: 14.

Synthesis of 6-[3-[2-chloro-6-(trifluoromethyl)benzoyl]-7-fluoro-indol-1-yl]pyridine-3-carboxylic acid (Compound 8)

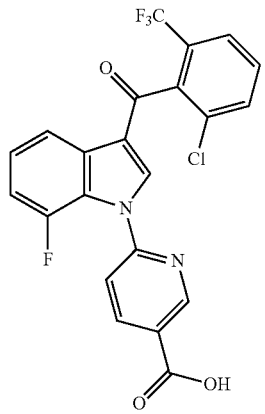 [SMILES: O=C(O)c1ccc(-n2cc(C(=O)c3c(Cl)cccc3C(F)(F)F)c3cccc(F)c32)nc1]

This compound was made using a similar method to that described above for Compound 4, yield 9%.

Synthesis of 4-[3-(2,6-dichlorobenzoyl)-7-methyl-indol-1-yl]benzoic acid (Compound 9)

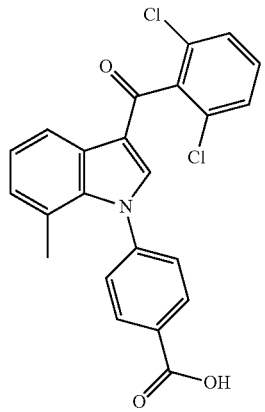 [SMILES: Cc1cccc2c(C(=O)c3c(Cl)cccc3Cl)cn(-c3ccc(C(=O)O)cc3)c12]

This compound was made using a similar method to that described above for Compound 4, yield 48%.

$^1$H NMR (600 MHz, DMSO) δ1.95 (s, 3H), 7.13 (d, 1H), 7.28 (t, 1H), 7.50 (m, 1H), 7.55-7.59 (m, 2H), 7.62-7.7 (m, 2H), 7.94 (s, 1H), 8.03-8.07 (m, 2H), 8.14 (s, 1H).

Expected Number of Hs: 15

Assigned Hs: 14.

Synthesis of 4-[3-[2-fluoro-6-(trifluoromethyl)benzoyl]-7-methyl-indol-1-yl]benzoic acid (Compound 11)

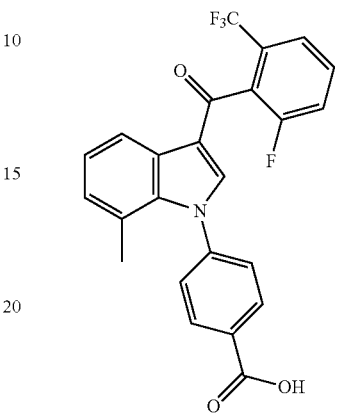

This compound was made using a similar method to that described above for Compound 4, yield 11%.

$^1$H NMR (600 MHz, DMSO) δ1.95 (s, 3H), 7.13 (d, 1H), 7.29 (t, 1H), 7.61-7.77 (m, 5H), 8.01 (s, 1H), 8.05 (d, 2H), 8.17 (broad s, 1H).

Synthesis of 4-[7-fluoro-3-[2-fluoro-6-(trifluoromethoxy)benzoyl]indol-1-yl]benzoic acid (Compound 12)

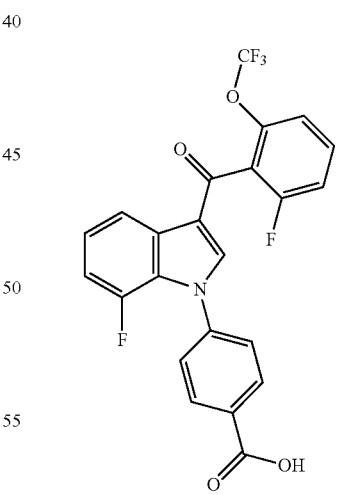

This compound was made using a similar method to that described above for Compound 4, yield 19%.

$^1$H NMR (600 MHz, DMSO) δ7.25 (m, 1H), 7.40 (m, 2H), 7.44 (t, 1H), 7.66-7.74 (m, 3H), 8.02-8.08 (m, 2H), 8.14 (d, 1H), 8.30 (s, 1H).

Expected Number of Hs: 12

Assigned Hs: 11

Synthesis of 3-fluoro-4-[7-fluoro-3-[2-fluoro-6-(trifluoromethoxy)benzoyl]indol-1-yl]benzoic acid
(Compound 13)

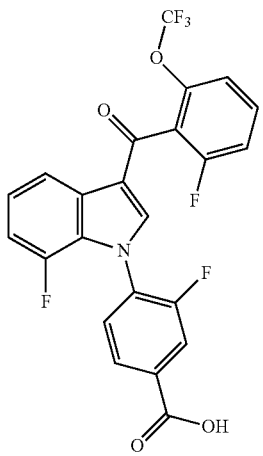 [SMILES: O=C(O)c1ccc(-n2cc(C(=O)c3c(F)cccc3OC(F)(F)F)c3cccc(F)c32)c(F)c1]

This compound was made using a similar method to that described above for Compound 4, yield 44%.

$^1$H NMR (600 MHz, DMSO) δ7.25 (m, 1H), 7.36-7.49 (m, 3H), 7.71 (m, 1H), 7.85 (t, 1H), 7.88-7.94 (m, 2H), 8.13 (d, 1H), 8.35 (s, 1H).

Expected Number of Hs: 11

Assigned Hs: 10.

Synthesis of 4-[3-[2-fluoro-6-(trifluoromethoxy)benzoyl]indol-1-yl]benzoic acid (Compound 14)

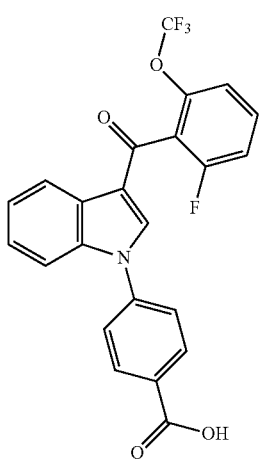 [SMILES: O=C(O)c1ccc(-n2cc(C(=O)c3c(F)cccc3OC(F)(F)F)c3ccccc32)cc1]

This compound was made using a similar method to that described above for Compound 4, yield 29%.

$^1$H NMR (600 MHz, DMSO) δ7.37-7.5 (m, 4H), 7.62-7.68 (m, 1H), 7.71 (m, 1H), 7.74-7.78 (m, 2H), 8.1-8.15 (m, 2H), 8.30 (s, 1H), 8.33 (s, 1H).

Expected Number of Hs: 13

Assigned Hs: 12.

Example 4

Synthesis of 4-[3-[[2-chloro-6-(trifluoromethyl)phenyl]methyl]indol-1-yl]-2-hydroxy-benzoic acid
(Compound 6)

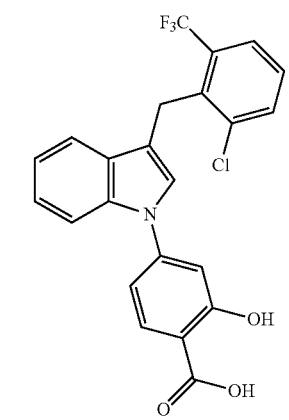 [SMILES: O=C(O)c1ccc(-n2cc(Cc3c(Cl)cccc3C(F)(F)F)c3ccccc32)cc1O]

Step 1

1H-indole (0.04 g, 0.34 mmol) was dissolved in methanol (2 mL) and 2-chloro-6-(trifluoromethyl)benzaldehyde (0.048 mL, 0.34 mmol) was added. Potassium hydroxide (0.057 g, 1.02 mmol) was added and the resulting mixture was stirred at ambient temperature for 1 week. The mixture was partitioned between water (2 mL) and dichloromethane (6 mL). The layers were separated in a phase separator and the organic layer was concentrated under reduced pressure to give a white solid (0.044 g, 40%).

The product is mainly a mixture of the hydroxyl compound and the methoxy compound and was used as such in the next step.

MS ESI$^-$ [M−H]$^-$ 324.1

Step 2

(2-chloro-6-(trifluoromethyl)phenyl)(1H-indol-3-yl)methanol (0.044 g, 0.14 mmol) was mixed with dichloromethane (0.5 mL) and triethylsilane (0.043 mL, 0.27 mmol). 2,2,2-trifluoroacetic acid (0.030 mL, 0.41 mmol) was added dropwise and the resulting mixture was stirred at ambient temperature for 3 days. The reaction mixture was partitioned between dichloromethane (6 mL) and sat. NaHCO$_3$ (1 mL). The layers were separated in a phase separator and the organic layer was concentrated under reduced pressure to give an off white solid (0.048 g, 115%). The crude material was used as such in the next step.

MS ESI$^+$ [M+H]$^+$308.1

Step 3

3-(2-chloro-6-(trifluoromethyl)benzyl)-1H-indole (0.048 g, 0.15 mmol), methyl 2-hydroxy-4-iodobenzoate (0.052 g, 0.19 mmol), 2-methylquinolin-8-ol (1.234 mg, 7.75 μmol), copper(I) iodide (4.43 mg, 0.02 mmol) were mixed as solids and diluted in DMSO (1 mL). potassium carbonate (0.075 g, 0.54 mmol) was added and the mixture was degassed by bubbling nitrogen for 15 mins. The mixture was stirred at 95° C. for 2 days.

Some water (0.5 mL) was added and the mixture was stirred 10 mins and then partitioned between 4 M HCl (2 mL) and ethyl acetate (7 ml). The layers were separated and the organic layer was washed with 50% saturated brine (3×1 mL). The organic layer was passed through a phase separator and concentrated under reduced pressure. The residue was dissolved in DMSO (1 mL), filtered and purified by reverse phase HPLC to give the product (0.0044 g, 6%).

1H NMR (600 MHz, DMSO) δ4.34 (s, 2H), 6.84 (s, 1H), 6.96 (d, 1H), 6.99-7.02 (m, 1H), 7.19-7.23 (m, 1H), 7.26-7.3 (m, 1H), 7.58 (t, 1H), 7.68 (d, 1H), 7.72 (d, 1H), 7.81-7.84 (m, 1H), 7.84-7.88 (m, 2H).

Expected Number of Hs: 15
Assigned Hs: 13.

Example 5

Synthesis of 4-[3-(2-fluoro-6-methoxy-benzoyl) indazol-1-yl]benzoic acid (Compound 10)

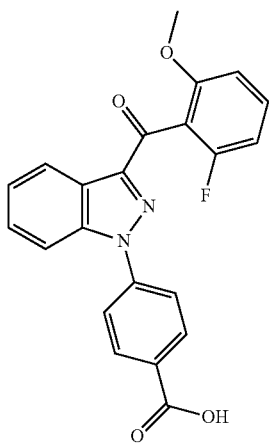 [SMILES: COc1cccc(F)c1C(=O)c1nn(-c2ccc(C(=O)O)cc2)c2ccccc12]

Step 1:

n-butyllithium (144 mg, 2.25 mmol)) was added portionwise to 3-iodo-1H-indazole (500 mg, 2.05 mmol) in Et$_2$O (20 mL) cooled to −78° C. under nitrogen, then tert-Butyllithium (262 mg, 4.10 mmol)) was added, after 20 minutes 2-fluoro-6-methoxybenzaldehyde (2.46 mmol) was added. The resulting mixture was stirred at room temperature for 4 hours.

The reaction mixture was quenched with ice water (50 mL), extracted with EtOAc (3×50 mL), the organic layer was dried over Na$_2$SO$_4$, filtered and evaporated to afford yellow solid. The crude product was purified by flash silica chromatography, elution gradient 5 to 50% EtOAc in petroleum ether. Pure fractions were evaporated to dryness to afford (2-fluoro-6-methoxyphenyl)(1H-indazol-3-yl)methanol as a yellow solid.

Yield 39%.

m/z (ES+), [M+H]+=273.

$^1$H NMR (300 MHz, DMSO-d6) δ12.65 (s, 1H), 7.90 (d, J=8.1 Hz, 1H), 7.47 (d, J=8.3 Hz, 1H), 7.41-7.22 (m, 2H), 7.07 (t, J=7.4 Hz, 1H), 6.88 (d, J=8.3 Hz, 1H), 6.85-6.68 (m, 1H), 6.59 (d, J=6.5 Hz, 1H), 5.75 (d, J=6.3 Hz, 1H), 3.79 (s, 3H).

Step 2:

Dess-Martin Periodinane (255 mg, 0.60 mmol) was added to (2-fluoro-6-methoxyphenyl)(1H-indazol-3-yl)methanol (0.55 mmol) in DCM (5 mL) cooled to 0° C. under nitrogen. The resulting mixture was stirred at room temperature for 3 hours.

The reaction mixture was quenched with saturated Na$_2$CO$_3$ (25 mL), extracted with DCM (3×25 mL), the organic layer was dried over Na$_2$SO$_4$, filtered and evaporated to afford yellow solid. The crude product was purified by flash silica chromatography, elution gradient 5 to 20% EtOAc in petroleum ether. Pure fractions were evaporated to dryness to afford (2-fluoro-6-methoxyphenyl)(1H-indazol-3-yl)methanone as a yellow solid.

Yield 70%.

m/z (ES+), [M+H]+=271.

$^1$H NMR (300 MHz, DMSO-d6) δ3.75 (d, J=5.6 Hz, 3H), 6.88-6.97 (m, 1H), 7.01 (d, J=8.4 Hz, 1H), 7.37-7.55 (m, 3H), 7.72 (dt, J=8.4, 1.0, 1.0 Hz, 1H), 8.24 (dt, J=8.2, 1.1, 1.1 Hz, 1H), 13.92 (s, 1H).

Step 3:

(2-fluoro-6-methoxyphenyl)(1H-indazol-3-yl)methanone (0.14 mmol), methyl 4-iodobenzoate (43.2 mg, 0.16 mmol), 2-Methyl 8-quinolinol (1,094 mg, 6.87 µmol), Copper(I) iodide (2.62 mg, 0.01 mmol) and Cs$_2$CO$_3$ (112 mg, 0.34 mmol) were mixed in DMSO (3 mL) and sealed into a microwave tube. The reaction was heated to 100° C. for 30 minutes in the microwave reactor and cooled to RT.

The reaction mixture was quenched with saturated NH$_4$Cl (25 mL), extracted with EtOAc (3×25 mL), the organic layer was dried over Na$_2$SO$_4$, filtered and evaporated to afford dark solid. The crude product was purified by flash silica chromatography, elution gradient 5 to 20% EtOAc in petroleum ether. Pure fractions were evaporated to dryness to afford methyl 4-(3-(2-fluoro-6-methoxyphenyl)-1H-indazol-1-yl)benzoate as a yellow solid.

Yield 67%.

m/z (ES+), [M+H]+=405.

$^1$H NMR (400 MHz, DMSO-d6) δ3.77 (s, 3H), 3.90 (s, 3H), 6.97 (t, 1H), 7.06 (d, 1H), 7.50-7.63 (m, 2H), 7.69 (m, 1H), 7.86-7.96 (m, 2H), 8.02 (d, 1H), 8.15-8.24 (m, 2H), 8.38 (d, 1H).

Step 4:

LiOH (3.94 mg, 0.16 mmol) was added to methyl 4-(3-(2-fluoro-6-methoxyphenyl)-1H-indazol-1-yl)benzoate (0.08 mmol) in THF (3 mL), water (1.500 mL). The resulting mixture was stirred at room temperature for 2 hours. The reaction mixture was acidified with 0.1 M HCl, extracted with EtOAc (3×20 mL), the organic layer was dried over Na$_2$SO$_4$, filtered and evaporated to afford grey solid. The crude product was purified by flash C18-flash chromatography, elution gradient 10 to 80% MeCN in water. Pure fractions were evaporated to dryness to afford 4-(3-(2,3-dichlorobenzoyl)-1H-indazol-1-yl)benzoic acid as a grey solid.

Yield 93%.

m/z (ES+), [M+H]+=391.

1H NMR (400 MHz, DMSO-d6) δ3.77 (s, 3H), 6.97 (t, 1H), 7.06 (d, 1H), 7.56 (m, 2H), 7.69 (m, 1H), 7.79-7.94 (m, 2H), 8.02 (d, 1H), 8.12-8.24 (m, 2H), 8.38 (d, 1H), 13.25 (s, 1H).

Example 6

Synthesis of 5-[3-(2,6-dichlorobenzoyl)indazol-1-yl]pyridine-2-carboxylic acid (Compound 15)

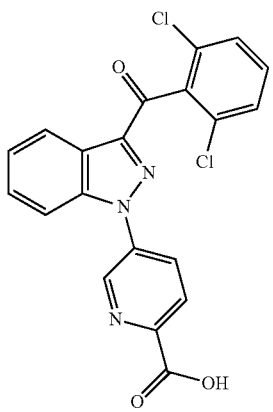 [SMILES: O=C(O)c1ccc(-n2nc(C(=O)c3c(Cl)cccc3Cl)c3ccccc32)cn1]

Step 1:

n-Butyllithium (289 mg, 4.51 mmol)) was added portionwise to 3-iodo-1H-indazole (1 g, 4.10 mmol) in Et$_2$O (20 mL) cooled to −78° C. under nitrogen, then tert-Butyllithium (525 mg, 8.20 mmol)) was added, after 20 minutes 2,6-dichlorobenzaldehyde (861 mg, 4.92 mmol) was added. The resulting mixture was stirred at room temperature for 4 hours.

The reaction mixture was quenched with ice water (50 mL), extracted with EtOAc (3×50 mL), the organic layer was dried over Na$_2$SO$_4$, filtered and evaporated to afford yellow solid. The crude product was purified by flash silica chromatography, elution gradient 5 to 50% EtOAc in petroleum ether. Pure fractions were evaporated to dryness to afford (2,6-dichlorophenyl)(1H-indazol-3-yl)methanol (500 mg, 41.6%) as a yellow solid.

m/z (ES$^+$), [M+H]$^+$=293.

Step 2:

Dess-Martin Periodinane (1241 mg, 2.93 mmol) was added to (2,6-dichlorophenyl)(1H-indazol-3-yl)methanol (780 mg, 2.66 mmol) in DCM (5 mL) cooled to 0° C. under nitrogen. The resulting mixture was stirred at room temperature for 3 hours.

The reaction mixture was quenched with saturated Na$_2$CO$_3$ (25 mL), extracted with DCM (3×25 mL), the organic layer was dried over Na$_2$SO$_4$, filtered and evaporated to afford yellow solid. The crude product was purified by flash silica chromatography, elution gradient 5 to 20% EtOAc in petroleum ether. Pure fractions were evaporated to dryness to afford (2,6-dichlorophenyl)(1H-indazol-3-yl)methanone (600 mg, 77%) as a pale yellow solid.

$^1$H NMR (400 MHz, DMSO-d$_6$) δ7.44 (t, 1H), 7.50-7.69 (m, 4H), 7.76 (d, 1H), 8.27 (d, 1H), 14.09 (s, 1H).

m/z (ES$^+$), [M+H]$^+$=291.

Step 3:

(2,6-dichlorophenyl)(1H-indazol-3-yl)methanone (50 mg, 0.17 mmol), methyl 5-bromopicolinate (44.5 mg, 0.21 mmol), 2-Methyl 8-quinolinol (1,367 mg, 8.59 μmol),Copper(I) iodide (3.27 mg, 0.02 mmol) and Cs$_2$CO$_3$ (140 mg, 0.43 mmol) were mixture in DMSO (5 mL) and sealed into a microwave tube. The reaction was heated to 120° C. for 40 minutes in the microwave reactor and cooled to RT.

The reaction mixture was quenched with saturated NH$_4$Cl (25 mL), extracted with EtOAc (3×25 mL), the organic layer was dried over Na$_2$SO$_4$, filtered and evaporated to afford dark solid. The crude product was purified by flash silica chromatography, elution gradient 5 to 20% EtOAc in petroleum ether. Pure fractions were evaporated to dryness to afford methyl 5-(3-(2,6-dichlorobenzoyl)-1H-indazol-1-yl)picolinate (30.0 mg, 41.0%) as a pale yellow solid.

$^1$HNMR (300 MHz, DMSO-d$_6$) δ3.94 (3H, s), 7.56-7.83 (5H, m), 8.12 (1H, d), 8.21-8.53 (3H, m), 9.14 (1H, d).

m/z (ES$^+$), [M+H]$^+$=426.

Step 4:

LiOH (2.81 mg, 0.12 mmol) was added to methyl 5-(3-(2,6-dichlorobenzoyl)-1H-indazol-1-yl)picolinate (25 mg, 0.06 mmol) in THF (4 mL), water (2.000 mL). The resulting mixture was stirred at room temperature for 2 hours. The reaction mixture was acidified with 0.1 M HCl, extracted with EtOAc (3×20 mL), the organic layer was dried over Na$_2$SO$_4$, filtered and evaporated to afford grey solid. The crude product was purified by preparative HPLC (Column: XSelect CSH Prep C18 OBD Column, 5 um, 19*150 mm; Mobile Phase A:Waters (0.1% FA), Mobile Phase B: ACN; Flow rate: 30 mL/min; Gradient: 47% B to 60% B in 7 min; 254/220 nm nm.) Fractions containing the desired compound were evaporated to dryness to afford 5-(3-(2,6-dichlorobenzoyl)-1H-indazol-1-yl)picolinic acid (20.00 mg, 83%) as a white solid.

$^1$HNMR (300 MHz, DMSO-d$_6$) δ7.50-7.82 (5H, m), 8.12 (1H, d), 8.28 (1H, d), 8.35 (1H, m), 8.43 (1H, d), 9.11 (1H, d), 12.83-14.12 (1H, m).

m/z (ES$^+$), [M+H]$^+$=412.

Example 7

Synthesis of 6-[3-(2,6-dichlorobenzoyl)indazol-1-yl]pyridine-3-carboxylic acid (Compound 16)

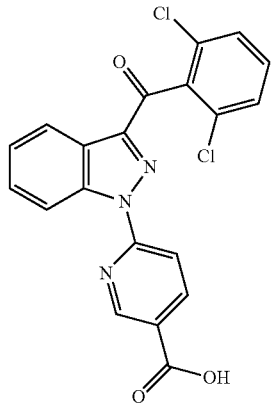 [SMILES: O=C(O)c1ccc(-n2nc(C(=O)c3c(Cl)cccc3Cl)c3ccccc32)nc1]

Compound 16 was prepared using a method in which the first two steps are identical to the method of Example 6. Steps 3 and 4 were performed in a similar manner to that used for Compound 15 but using an ester of 6-bromopyridine-3-carboxylic acid in place of the methyl 5-bromopicolinate.

Step 3:

Yield 68%.

$^1$HNMR (300 MHz, DMSO-d$_6$) δ3.92 (3H, s), 7.58-7.91 (6H, m), 8.42 (1H, d), 8.51 (1H, m), 8.91 (1H, d), 9.11-9.22 (1H, m).

Step 4:
Yield 84%.
m/z (ES+), [M+H]+=412.
¹HNMR (300 MHz, DMSO-d₆) δ7.56-7.75 (4H, m), 7.76-7.92 (2H, m), 8.42 (1H, d), 8.50 (1H, m), 8.92 (1H, d), 9.13 (1H, d), 13.53 (1H, s).

Example 8

Synthesis of 6-[3-[(2,6-dichlorophenyl)methyl]indazol-1-yl]pyridine-3-carboxylic acid (Compound 17)

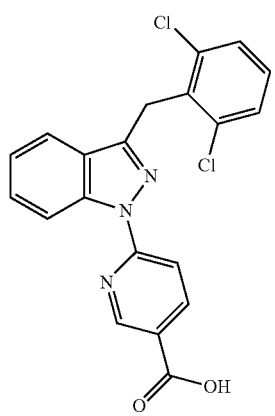 [SMILES: O=C(O)c1ccc(-n2nc(Cc3c(Cl)cccc3Cl)c3ccccc32)nc1]

Step 1:
Step 1 is identical to Step 1 of Example 6 above.
Step 2:
TFA (0.526 mL, 6.82 mmol) was added to (2,6-dichlorophenyl)(1H-indazol-3-yl)methanol (200 mg, 0.68 mmol), Triethylsilane (793 mg, 6.82 mmol) in THF (10 mL) under nitrogen. The resulting mixture was stirred at 60° C. for 12 hours.

The reaction mixture was basified with saturated NaHCO₃, extracted with EtOAc (3×25 mL), the organic layer was dried over Na₂SO₄, filtered and evaporated to afford yellow solid. The crude product was purified by flash silica chromatography, elution gradient 0 to 20% EtOAc in petroleum ether. Pure fractions were evaporated to dryness to afford 3-(2,6-dichlorobenzyl)-1H-indazole (130 mg, 68.8%) as a yellow solid.

¹HNMR (300 MHz, DMSO) δ4.56 (2H, s), 7.08 (1H, t), 7.35 (2H, q), 7.50 (3H, t), 7.62 (1H, d), 12.69 (1H, s).
m/z (ES+), [M+H]+=277.
Step 3:
Performed as for Example 6, step 3.
Yield 47%.
1HNMR (300 MHz, DMSO) δ3.90 (3H, s), 4.71 (2H, s), 7.31-7.55 (2H, m), 7.54-7.77 (3H, m), 7.83 (2H, m), 8.40 (1H, m), 8.80 (1H, d), 9.05 (1H, d).
Step 4:
Performed as for Example 6, step 4.
Yield 71%.
m/z (ES+), [M+H]+=398.
¹HNMR (300 MHz, DMSO-d₆) δ4.70 (2H, s), 7.35-7.44 (2H, m), 7.56-7.65 (3H, m), 7.76-7.86 (2H, m), 8.37 (1H, m), 8.79 (1H, d), 9.02 (1H, d), 13.29 (1H, s)

Example 9

Synthesis of 4-[3-[[2-chloro-6-(trifluoromethyl)phenyl]methyl]indazol-1-yl]benzoic acid (Compound 18)

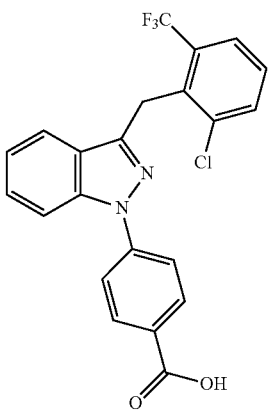 [SMILES: O=C(O)c1ccc(-n2nc(Cc3c(Cl)cccc3C(F)(F)F)c3ccccc32)cc1]

Step 1:
Performed as for Example 6, step 1 but using 2-chloro-6-trifluoromethyl benzaldehyde.
Yield 45%.
m/z (ES+), [M+H]+=327.
Step 2:
Either performed as for Example 8: step 2 or as follows.

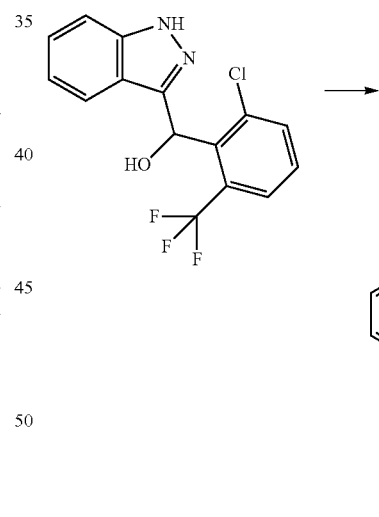

Iodine (1.13 g, 4.46 mmol) was added to a solution of [2-chloro-6-(trifluoromethyl)phenyl](1H-indazol-3-yl)methanol (0.49 g, 1.49 mmol) in acetic acid (9 ml) followed by hypophosphorus acid soln 50% (1188.6 µl, 10.86 mmol). The reaction was heated to 150° C. in the microwave and allowed to stir for 5 minutes.

The reaction was left to stand at room temperature overnight. The reaction mixture was concentrated in vacuo to remove acetic acid. The residue was diluted with water (~15 ml) and the pH of the resultant solution adjusted to pH ~8 with 5 M sodium hydroxide solution. The aqueous was then extracted with ethyl acetate (2×~20 ml) and the combined organic layers were washed with brine (~50 ml), dried over sodium sulphate and evaporated to give 448 mg of as a pale yellow powder $^1$H NMR (500 MHz, DMSO-d$_6$) δ=12.60 (s, 1H), 7.85-7.78 (m, 2H), 7.60-7.54 (m, 2H), 7.46 (d, J=8.4, 1H), 7.35-7.29 (m, 1H), 7.09-7.03 (m, 1H), 4.53 (s, 2H).

Yield 70%.

m/z (ES$^+$), [M+H]$^+$=311.

$^1$HNMR (300 MHz, DMSO-d$_6$) δ4.55 (2H, s), 7.08 (1H, t), 7.28-7.41 (1H, m), 7.48 (1H, d), 7.58 (2H, t), 7.83 (2H, t), 12.64 (1H, s). 4.55 (2H, s), 7.08 (1H, t), 7.28-7.41 (1H, m), 7.48 (1H, d), 7.58 (2H, t), 7.83 (2H, t), 12.64 (1H, s).

Step 3:

Performed as for Example 6, step 3.

Yield 49%.

$^1$HNMR (400 MHz, DMSO-d$_6$) δ3.87 (3H, d), 4.62 (2H, d), 7.30 (1H, m), 7.61 (2H, m), 7.73-7.91 (4H, m), 7.91-8.03 (2H, m), 8.05-8.19 (2H, m).

Step 4:

Performed as for Example 6, step 4.

m/z (ES$^+$), [M+H]$^+$=431

$^1$HNMR (300 MHz, DMSO-d$_6$) δ4.67 (2H, s), 7.32 (1H, t), 7.53-7.64 (2H, m), 7.75 (2H, d), 7.81-7.89 (3H, m), 7.96 (1H, d), 8.07 (2H, d), 13.05 (1H, s).

Other Compounds

The following compounds were prepared by methods analogous to those described above:

LCMS data: Retention time 4.42; m/z (ES$^+$), [M+H]$^+$=431

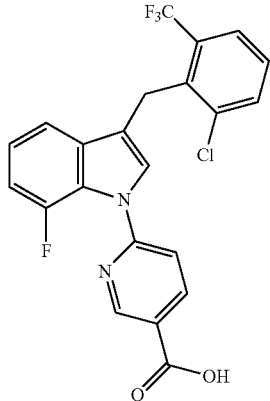

(Compound 20)

6-[3-[[2-chloro-6-(trifluoromethyl)phenyl]methyl]-7-fluoro-indol-1-yl]pyridine-3-carboxylic acid 1H NMR (500 MHz, DMSO-d6) δ8.77 (d, J=1.7 Hz, 1H), 8.20 (dd, J=8.3, 2.0 Hz, 1H), 7.85 (dd, J=20.4, 8.0 Hz, 2H), 7.62-7.56 (m, 2H), 7.35 (dd, J=8.2, 5.6 Hz, 1H), 7.21 (td, J=7.9, 4.4 Hz, 1H), 7.12 (dd, J=12.9, 7.8 Hz, 1H), 6.90 (s, 1H), 4.35 (s, 2H).

LCMS data: Retention time 4.36; m/z (ES$^+$), [M+H]$^+$=449.

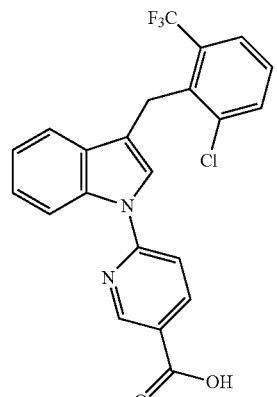

(Compound 19)

6-[3-[[2-chloro-6-(trifluoromethyl)phenyl]methyl]indol-1-yl]pyridine-3-carboxylic acid 1H NMR (500 MHz, DMSO-d6) δ8.81 (d, J=1.7 Hz, 1H), 8.30 (d, J=8.3 Hz, 1H), 8.18 (dd, J=8.4, 2.1 Hz, 1H), 7.87 (dd, J=15.8, 8.0 Hz, 2H), 7.72 (d, J=7.8 Hz, 1H), 7.60 (t, J=8.0 Hz, 1H), 7.45 (d, J=8.4 Hz, 1H), 7.30 (t, J=7.7 Hz, 1H), 7.22 (t, J=7.5 Hz, 1H), 7.11 (s, 1H), 4.35 (s, 2H).

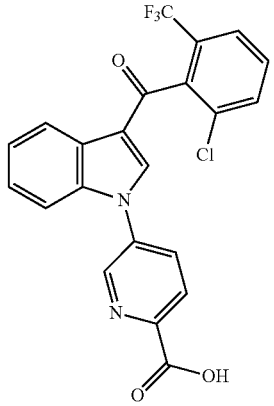

(Compound 21)

5-[3-[2-chloro-6-(trifluoromethyl)benzoyl]indol-1-yl]pyridine-2-carboxylic acid

1H NMR (500 MHz, DMSO-d6) δ 8.74-8.55 (m, 1H), 8.49-8.13 (m, 2H), 8.11-7.96 (m, 2H), 7.98-7.83 (m, 2H), 7.75 (t, J=8.1 Hz, 1H), 7.62-7.52 (m, 1H), 7.48-7.31 (m, 2H).

LCMS: Retention time: 3.4; m/z (ES$^+$), [M+H]$^+$=445.

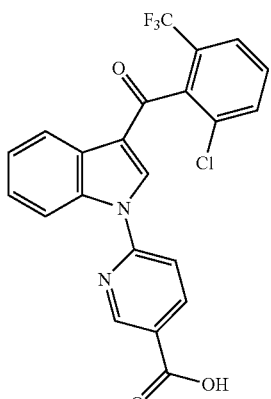

6-[3-[2-chloro-6-(trifluoromethyl)
benzoyl]indol-1-yl]pyridine-3-
carboxylic acid
(Compound 22)

1H NMR (500 MHz, DMSO-d6) δ8.93 (d, J=1.7 Hz, 1H), 8.49-8.22 (m, 4H), 8.00-7.87 (m, 2H), 7.78 (t, J=8.0 Hz, 1H), 7.70 (d, J=7.8 Hz, 1H), 7.50-7.33 (m, 2H).

LCMS: Retention time: 3.73; m/z (ES$^+$), [M+H]$^+$=445

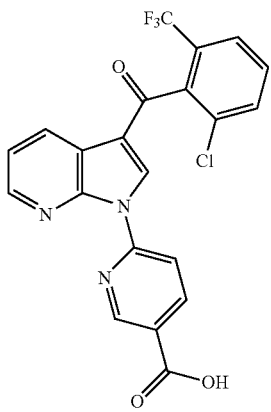

6-[3-[2-chloro-6-(trifluoromethyl)
benzoyl]pyrrolo[2,3-b]pyridin-1-
yl]pyridine-3-carboxylic acid
(Compound 23)

1H NMR (500 MHz, DMSO-d6) δ=9.03-8.95 (m, 2H), 8.93-8.57 (m, 3H), 8.54 (dd, J=8.7, 2.0, 1H), 8.02 (d, J=8.0, 1H), 7.97 (d, J=7.9, 1H), 7.84 (t, J=8.1, 1H), 7.61-7.54 (m, 1H).

LCMS: Retention time: 3.79; m/z (ES$^+$), [M+H]$^+$=446.

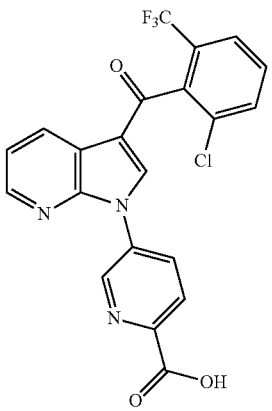

5-[3-[2-chloro-6-(trifluoromethyl)
benzoyl]pyrrolo[2,3-b]pyridin-1-
yl]pyridine-2-carboxylic acid
(Compound 24)

1H NMR (500 MHz, DMSO-d6) δ=8.93-8.85 (m, 1H), 8.84-8.43 (m, 3H), 8.17-8.06 (m, 1H), 7.98 (d, J=8.4, 1H), 7.95 (d, J=8.0, 1H), 7.91 (d, J=8.2, 1H), 7.78 (t, J=8.2, 1H), 7.54-7.45 (m, 1H).

LCMS: Retention time: 3.28; m/z (ES$^+$), [M+H]$^+$=446.

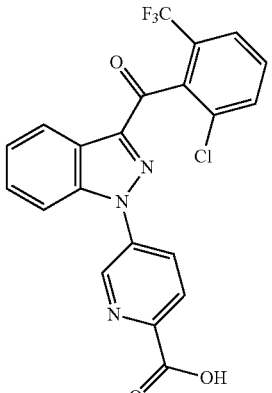

5-[3-[2-chloro-6-(trifluoromethyl)
benzoyl]indazol-1-yl]pyridine-2-
carboxylic acid
(Compound 25)

1H NMR (500 MHz, DMSO-d6) δ=8.71 (d, J=2.3, 1H), 8.40 (d, J=7.9, 1H), 8.11 (dd, J=8.4, 2.5, 1H), 8.07 (d, J=8.3, 1H), 8.00-7.92 (m, 3H), 7.83-7.79 (m, 1H), 7.71 (ddd, J=8.4, 7.0, 1.0, 1H), 7.64-7.58 (m, 1H).

LCMS: Retention time: 3.67; m/z (ES$^+$), [M+H]$^+$=446.

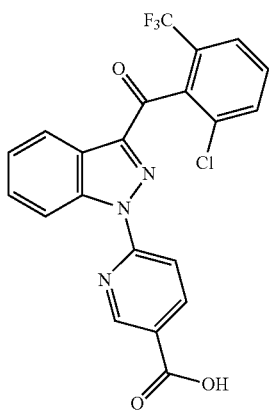

(Compound 26)

6-[3-[2-chloro-6-(trifluoromethyl)benzoyl]indazol-1-yl]pyridine-3-carboxylic acid 1H NMR (500 MHz, DMSO-d6) δ=8.99-8.93 (m, 1H), 8.83 (d, J=8.6, 1H), 8.37 (d, J=7.9, 1H), 8.27 (dd, J=8.4, 2.0, 1H), 8.01 (d, J=8.0, 1H), 7.97 (d, J=7.9, 1H), 7.88-7.82 (m, 1H), 7.73 (ddd, J=8.5, 7.1, 1.1, 1H), 7.62-7.57 (m, 1H), 7.51 (d, J=8.3, 1H).

LCMS: Retention time 4.19; m/z (ES$^+$), [M+H]$^+$=446.

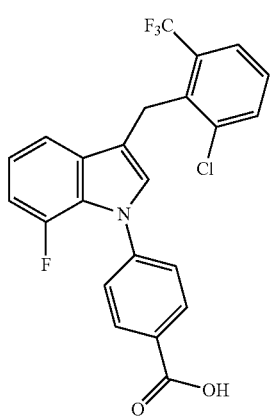

(Compound 27)

4-[3-[[2-chloro-6-(trifluoromethyl)phenyl]methyl]-7-fluoro-indol-1-yl]benzoic acid 1H NMR (250 MHz, DMSO) δ4.35 (s, 2H), 6.78 (s, 1H), 6.99-7.25 (m, 2H), 7.48 (dd, 2H), 7.53-7.62 (m, 2H), 7.83 (t, 2H), 7.98 (d, 2H).

LCMS: Retention time: 4.95; m/z (ES$^+$), [M+H]$^+$=448.

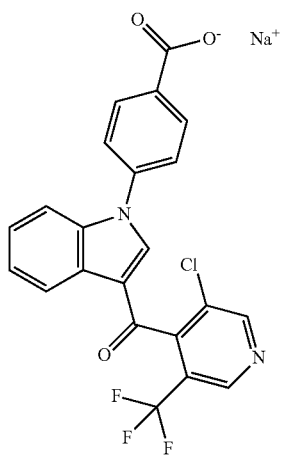

(Compound 28)

sodium 4-{3-[3-chloro-5-(trifluoromethyl)pyridine-4-carbonyl]indol-1-yl}benzoate 1H NMR (500 MHz, DMSO) δ7.32-7.40 (m, 4H), 7.50-7.56 (m, 1H), 7.94 (d, 2H), 8.31 (d, 2H), 9.02 (d, 2H).

LCMS: Retention time: 3.57; m/z (ES$^+$), [M+H]$^+$=445.1

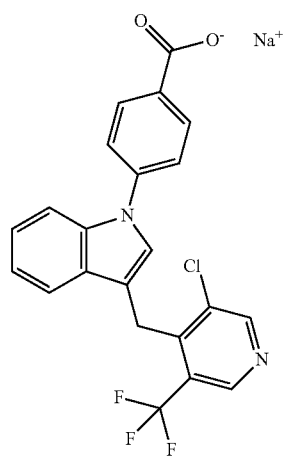

(Compound 29)

sodium 4-(3-{[3-chloro-5-(trifluoromethyl)pyridine-4-yl]methyl}indol-1-yl)benzoate 1H NMR (500 MHz, DMSO) δ4.36 (s, 2H), 6.96 (s, 1H), 7.18 (t, 1H), 7.21-7.26 (m, 1H), 7.28-7.33 (m, 2H), 7.57 (d, 1H), 7.74 (d, 1H), 7.89-7.96 (m, 2H), 8.96 (d, 2H). LCMS: Retention time: 4.03; m/z (ES$^+$), [M+H]$^+$=431.1.

(Compound 30)

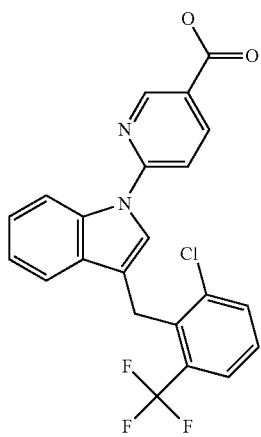

6-(3-{[2-chloro-6-(trifluoromethyl)
phenyl]methyl]indazol-1-yl)
pyridine-3-carboxylic acid 1H NMR (500 MHz, DMSO-d6) δ=9.13 (dd, J=2.2, 0.6, 1H), 8.58 (dd, J=8.5, 2.3, 1H), 8.30 (dd, J=8.5, 0.6, 1H), 7.93 (d, J=7.6, 1H), 7.88 (d, J=7.9, 1H), 7.69 (t, J=8.0, 1H), 7.63 (d, J=8.9, 1H), 7.21 (ddd, J=8.8, 6.6, 0.8, 1H), 6.78-6.71 (m, 1H), 6.07 (d, J=8.8, 1H), 5.17 (s, 2H).

LCMS: Retention time: 3.9; m/z (ES+), [M+H]+=432.1

(Compound 31)

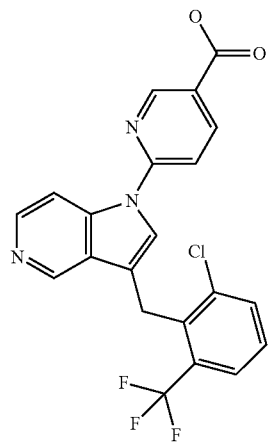

4-(3-{[2-chloro-6-(trifluoromethyl)
phenyl[methyl}pyrrolo[3,2-c]pyridin-1-
yl)benzoic acid 1H NMR (500 MHz, DMSO-d6) δ=8.92 (d, J=0.7, 1H), 8.29 (d, J=5.8, 1H), 8.00-7.93 (m, 2H), 7.90-7.80 (m, 2H), 7.59 (t, J=8.0, 1H), 7.52 (dd, J=5.8, 0.9, 1H), 7.38-7.30 (m, 2H), 6.96 (d, J=1.3, 1H), 4.50-4.39 (m, 1H).

LCMS: Retention time: 2.23; m/z (ES+), [M+H]+=431.

(Compound 32)

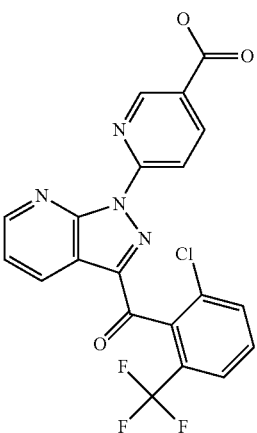

6-{3-[2-chloro-6-
(trifluoromethyl)benzoyl]pyrazolo[3,4-
b]pyridin-1-yl}pyridine-3-carboxylic acid 1H NMR (500 MHz, DMSO-d6) δ=8.93-8.89 (m, 1H), 8.85 (dd, J=4.5, 1.6, 1H), 8.81-8.75 (m, 1H), 8.34 (dd, J=8.2, 2.1, 1H), 8.01 (d, J=8.2, 1H), 7.97 (d, J=7.9, 1H), 7.93 (d, J=8.2, 1H), 7.84 (t, J=8.1, 1H), 7.67 (dd, J=8.1, 4.5, 1H).

LCMS: Retention time 3.45; m/z (ES+), [M+H]+=447.

(Compound 33)

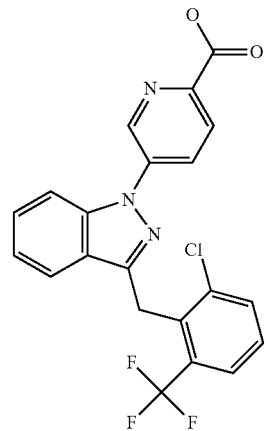

5-(3-{[2-chloro-6-(trifluoromethyl)
phenyl]methyl}indazol-1-yl)
pyridine-2-carboxylic acid 1H NMR (500 MHz, DMSO-d6) δ=8.68 (d, J=2.1, 1H), 8.04-7.96 (m, 2H), 7.89-7.80 (m, 4H), 7.60 (t, J=8.0, 1H), 7.54 (ddd, J=8.3, 7.0, 0.9, 1H), 7.30 (t, J=7.5, 1H), 4.67 (s, 2H).

LCMS: retention time: 3.96; m/z (ES+), [M+H]+=432.2.

(Compound 34)

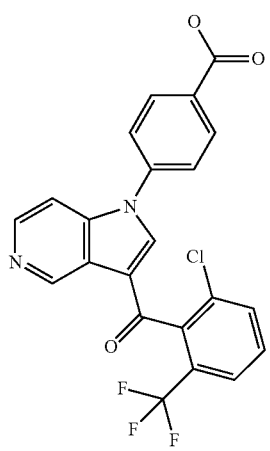

4-{3-[2-chloro-6-(trifluoromethyl)benzoyl]pyrrolo[3,2-c]pyridin-1-yl}benzoic acid 1H NMR (500 MHz, DMSO-d6) δ=9.52 (s, 1H), 8.47 (d, J=5.6, 1H), 8.35 (s, 1H), 8.00 (d, J=8.4, 2H), 7.97-7.86 (m, 2H), 7.77 (t, J=8.2, 1H), 7.61 (dd, J=5.8, 0.8, 1H), 7.49-7.41 (m, 2H).

LCMS: retention time 2.08; m/z (ES$^+$), [M+H]$^+$=445.1

(Compound 35)

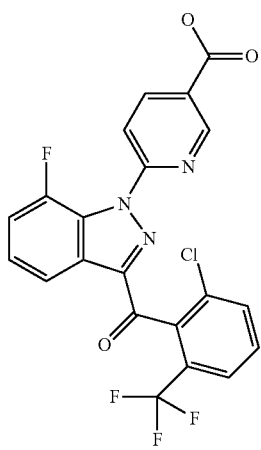

6-{3-2[chloro-6-(trifluoromethyl)benzoyl]-7-fluoroindazol-1-yl}pyridine-3-carboxylic acid 1H NMR (500 MHz, DMSO-d6) δ=8.91-8.85 (m, 1H), 8.30 (dd, J=8.1, 2.1, 1H), 8.21 (d, J=7.7, 1H), 8.01-7.91 (m, 2H), 7.81 (t, J=8.1, 1H), 7.60-7.46 (m, 3H);

LCMS: retention time 3.93; m/z (ES$^+$), [M+H]$^+$=464.1

(Compound 36)

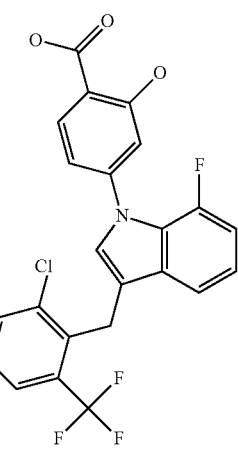

4-(3-{[2-chloro-6-(trifluoromethyl)phenyl]methyl}-7-fluoroindol-1-yl)-2-hydroxybenzoic acid 1H NMR (500 MHz, DMSO) δ4.34 (s, 2H), 6.79 (s, 1H), 6.92 (d, 2H), 7.10 (m, 1H), 7.19 (td, 1H), 7.58 (dd, 2H), 7.81 (dd, 2H), 7.85 (d, 1H).

LCMS: retention time: 4.8; m/z (ES$^+$), [M+H]$^+$=463.9

BIOLOGICAL EXAMPLES

Example 10

FRET Assay

This assay measures the binding of the SRC-1 peptide to the RORγ ligand binding domain in the presence and absence of compound. The SRC-1 peptide was tagged with the streptavidin-europium and the RORγ ligand binding domain was tagged with strepavidin-APC. Labelled RORγ ligand binding domain (50 nM) and SRC-1 peptide (80 nM) were incubated in buffer containing 50 mM MOPS pH7.4, 50 mM potassium fluoride, 50 μM CHAPS (0.003%|), 0.1 mg/ml BSA (0.01%) and 50 mM DTT for 1 hour in the dark at room temperature n the presence and absence of compound.

Inverse agonists of coactivator binding will prevent a proximity based energy transfer between from Eu to APC resulting in decrease in the FRET signal when measured at 665 nM.

Assay Protocol

The assay was run in black 384 well plates (Greiner cat no: 784900). Various concentrations of test ligands in 0.1 microliters DMSO were dispensed to assay plates using an Labcyte Echo acoustic dispenser. Two pre-mixes were prepared and incubated for 1 hr at room temp in the dark. Pre-mix 1 comprised 100 nM Protein (Biotinylated HN-Avi-MBP-TCS-hRORg (258-518)) and 60 nM Streptavidin APC in assay buffer, 50 mM MOPS pH7.4, 50 mM KF, 0.003% (w/v) CHAPS, 10 mM DTT and 0.01% (w/v) BSA and pre-mix 2 comprised 160 nM biotinylated SRC-1 peptide (NCOA1-677-700) and 20 nM Europium-W8044 labelled Streptavidin in assay buffer.

Five microliters of pre-mix 2 was dispensed to assay plates containing test compound and incubated for 15 minutes prior to adding five microliters of pre-mix 1. Plates were incubated at room temperature for 1 hour in the dark, prior to reading in a Pherastar multi-mode plate reader using HTRF filter set (ex 320, em 612 and 665). The FRET signal at 665 nM was divided by the signal at 612 nM and multiplied by 10,000 to generate a signal ratio value for each well. The raw data was transformed to % effect using the equation:

Compound % effect=100*[(X−min)/(max−min)], where X represents the normalized value for the compound based on the Min (vehicle) and Max (reference compound) inhibition control.

The concentration of test ligand that inhibited the activity by 50% (i.e., the $IC_{50}$) was calculated by plotting the % effect versus test ligand concentration and fitting the data using the Genedata Screener Smart fit algorithm. The results for Compounds 1-14 are shown in Table 1.

TABLE 1

Mean $IC_{50}$ values for compounds in RORγ FRET assay

| Compound No | RORγ FRET - Mean $IC_{50}$ (μM) |
| --- | --- |
| 1 | 0.1962 |
| 2 | 0.07176 |
| 3 | 1.371 |
| 4 | 0.8977 |
| 5 | 0.3803 |
| 6 | 0.01895 |
| 7 | 0.5752 |
| 8 | 0.2122 |
| 9 | 1.348 |
| 10 | 0.6294 |
| 11 | 1.237 |
| 12 | 0.2474 |
| 13 | 0.3731 |
| 14 | 0.5143 |
| 15 | 15.84 |
| 16 | 0.25 |
| 19 | 0.79 |
| 20 | 0.63 |
| 22 | 1 |
| 23 | 1.26 |
| 22 | 12.6 |
| 26 | 0.13 |
| 27 | 0.13 |

Example 11

Human Th17 Cell Differentiation Assay

Human CD4+CCR6+ T cells were isolated from peripheral blood mononuclear cells by positive selection. These cells were incubated in a cocktail of cytokines (1 ng/mL TGF-β1, 10 ng/mL IL-1β, 50 ng/mL IL-23, 10 ng/mL IL-6 and 5 ng/mL IL-2) and antiCD2/CD3/28 beads to induce polarisation and expansion of CD4+ IL-17+ T cells ($T_H17$ cells) over a period of 4 days in the presence and absence of compound.

The concentration of IL17A were measured in the extracellular media by sandwich ELISA. Compounds that inhibited $T_H17$ cell differentiation and expansion reduced the levels of IL-17A in the extracellular media. The results are shown in Table 2.

TABLE 2

Mean $IC_{50}$ values for compounds in $T_H17$ cell differentiation assay

| Compound No | Inhibition of $T_H17$ cell differentiation - Mean $IC_{50}$ (μM) |
| --- | --- |
| 1 | 0.1415 |
| 2 | 0.03357 |
| 3 | 0.3563 |
| 4 | 1.49 |
| 5 | 0.8212 |
| 6 | 0.004806 |
| 7 | 0.4984 |
| 8 | 0.03947 |
| 9 | 1.598 |
| 10 | 0.4548 |
| 12 | 0.1925 |
| 13 | 0.1812 |
| 14 | 0.3378 |

The invention claimed is:

1. A compound of formula (I):

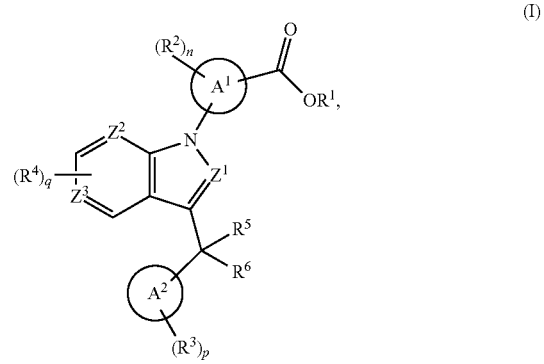

wherein:
$Z^1$ is $CR^7$;
each $R^7$ is independently selected from the group consisting of H, $C_{1-4}$ alkyl, $C_{1-4}$ haloalkyl, halo, CN, and $NO_2$;
$Z^2$ and $Z^3$ are each $CR^{10}$;
each $R^{10}$ is independently selected from the group consisting of H, $R^{15}$, and $C_{1-4}$ alkyl optionally substituted with one or more $R^{15}$;
wherein each $R^{15}$ is independently selected from the group consisting of halo, CN, $NO_2$, $OR^{16}$, $C(=O)R^{16}$, $C(=O)OR^{16}$, $C(=O)NR^{16}R^{17}$, $SR^{16}$, $S(=O)R^{16}$, $S(=O)_2R^{16}$, $NR^{16}R^{17}$, and $NR^{18}C(=O)R^{16}$;
wherein:
each one of $R^{16}$ and $R^{17}$ is independently selected from the group consisting of hydrogen, $C_{1-6}$ alkyl optionally substituted with one or more halo substituents, $C_{3-8}$ cycloalkyl optionally substituted with one or more halo substituents, and $C_{5-7}$ heterocyclyl optionally substituted with one or more halo substituents; and
$R^{18}$ is H or C1-4 alkyl;
$A^1$ is pyridyl;
$R^1$ is H or $C_{1-6}$ alkyl optionally substituted with one or more substituents selected from the group consisting of halo, OH, and phenyl, wherein the phenyl group is optionally substituted with 1 to 3 substituents independently selected from the group consisting of OH, CN, $NO_2$, halo, $C_{1-4}$ alkyl, and $C_{1-4}$ haloalkyl;
each $R^2$ is independently selected from the group consisting of halo, CN, $NO_2$, $OR^{11}$, $NR^{11}R^{12}$, and $C_{1-6}$ alkyl optionally substituted with one or more substituents selected from the group consisting of phenyl, halo, CN, $NO_2$, $OR^{11}$, and $NR^{11}R^{12}$,
  wherein each one of $R^{11}$ and $R^{12}$ is independently selected from the group consisting of hydrogen, $C_{1-4}$ alkyl optionally substituted with one or more halo substituents, and $C_{3-8}$ cycloalkyl optionally substituted with one or more halo substituents;
n is 0, 1, 2, 3, or 4;
$A^2$ is phenyl;
each $R^3$ is independently selected from the group consisting of halo, CN, $NO_2$, OH, $OR^{13}$, $NR^{13}R^{14}$, $C_{1-6}$ alkyl, $C_{2-6}$ alkenyl, $C_{3-8}$ cycloalkyl, and $C_{5-7}$ heterocyclyl, wherein the alkyl, alkenyl, cycloalkyl, or heterocyclyl group is optionally substituted with one or more substituents selected from the group consisting of phenyl, halo, CN, $NO_2$, OH, $OR^{13}$ and $NR^{13}R^{14}$;
  wherein:
    each $R^{13}$ and $R^{14}$ is independently selected from the group consisting of hydrogen, $C_{1-4}$ alkyl, $C_{3-8}$ cycloalkyl, and $C_{5-7}$ heterocyclyl, any of which being optionally substituted with one or more substituents selected from the group consisting of halo, $C_{1-4}$ alkoxy, and oxo; or
    $R^{13}$ and $R^{14}$ together with the nitrogen atom to which they are attached may form a 4-7 membered heterocyclic ring optionally containing one or more further heteroatoms selected from the group consisting of N, O, and S and optionally substituted with one or more substituents selected from the group consisting of halo, $C_{1-4}$ alkoxy, and oxo;
p is 0, 1, 2, 3, 4 or 5;
each $R^4$ is independently selected from the group consisting of $R^{15}$ and $C_{1-4}$ alkyl optionally substituted with one or more $R^{15}$;
where $R^{15}$ is as defined above;
q is 0, 1, or 2;
each of $R^5$ and $R^6$ is H, or $R^5$ and $R^6$ together form =O;
or a pharmaceutically or veterinarily acceptable salt, solvate-stereoisomer or hydrate thereof, or a deuterated or tritiated variant thereof.

2. The compound of claim 1, wherein:
A is 2-pyridyl and the C(=O)$OR^1$ group is at the 5-position of the pyridine ring.

3. The compound of claim 1, wherein $R^1$ is H, $C_{1-6}$ alkyl, or benzyl.

4. The compound of claim 1, wherein n is 0, 1, or 2, and $R^2$, when present, is chloro, fluoro, methyl, or trifluoromethyl; or wherein n is 0, 1, or 2, and $R^2$, when present, is OH.

5. The compound of claim 1, wherein n is 0 or 1.

6. The compound of claim 1, wherein each $R^3$ is independently selected from the group consisting of halo, CN, $NO_2$, OH, $NR^{12}R^{13}$, and $C_{1-4}$ alkyl optionally substituted with one or more substituents selected from the group consisting of phenyl, halo, CN, $NO_2$, OH, and $NR^{13}R^{14}$;
  where each $R^{13}$ and $R^{14}$ is independently selected from the group consisting of hydrogen, $C_{1-2}$ alkyl optionally substituted with one or more halo substituents, and $C_{3-7}$ cycloalkyl optionally substituted with one or more halo substituents.

7. The compound of claim 1, wherein p is 2, one of the $R^3$ groups is halo, and the other $R^3$ group is trifluoromethyl.

8. The compound of claim 1, wherein $R^4$ is chloro or fluoro and q is 1; or wherein q is 0 and $R^4$ is not present.

9. The compound of claim 1, wherein $A^1$ is 3-pyridyl and the C(=O)$OR^1$ group is at the 6-position of the pyridine ring.

10. The compound of claim 1, which is selected from the group consisting of:
  6-[3-[2-chloro-6-(trifluoromethyl)benzoyl]-7-fluoro-indol-1-yl]pyridine-3-carboxylic acid (Compound 8);
  6-[3-[[2-chloro-6-(trifluoromethyl)phenyl]methyl]indol-1-yl]pyridine-3-carboxylic acid (Compound 19);
  6-[3-[[2-chloro-6-(trifluoromethyl)phenyl]methyl]-7-fluoro-indol-1-yl]pyridine-3-carboxylic acid (Compound 20);
  5-[3-[2-chloro-6-(trifluoromethyl)benzoyl]indol-1-yl]pyridine-2-carboxylic acid (Compound 21);
  6-[3-[2-chloro-6-(trifluoromethyl)benzoyl]indol-1-yl]pyridine-3-carboxylic acid (Compound 22);

$C_{1-6}$ alkyl and benzyl esters thereof; and, their pharmaceutically or veterinarily acceptable salts or free acids, solvates or hydrates or a deuterated or tritiated variant thereof, or any-stereoisomer thereof.

11. A pharmaceutical or veterinary composition comprising at least one compound of claim 1 and a pharmaceutically or veterinarily acceptable excipient or carrier.

12. The composition of claim 11, further comprising an additional active agent for the treatment of a disease or condition selected from the group consisting of asthma, chronic obstructive pulmonary disease (COPD), bronchitis, allergic diseases, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease, and scleritis.

13. A method of treating an inflammatory or autoimmune disease, the method comprising administering to a patient in need of such treatment an effective amount of at least one compound of claim 1, wherein the inflammatory or autoimmune disease is selected from the group consisting of asthma, chronic obstructive pulmonary disease (COPD), bronchitis, allergic diseases, cystic fibrosis, lung allograft rejection, multiple sclerosis, rheumatoid arthritis, juvenile rheumatoid arthritis, osteoarthritis, ankylosing spondylitis, systemic lupus erythematosus, psoriasis, Hashimoto's disease, pancreatitis, autoimmune diabetes, autoimmune ocular disease, ulcerative colitis, Crohn's disease, inflammatory bowel disease (IBD), Sjorgen's syndrome, Behcet's disease, optic neuritis, type I diabetes, neuromyelitis optica, myasthenia gravis, uveitis, Guillain-Barre syndrome, psoriatic arthritis, Graves' disease, and scleritis.

14. A method of preparing a compound of claim 1, the method comprising:
  a. for compounds of formula (I) in which $R^1$ is hydrogen:
    hydrolysing of a compound of formula (I) wherein $R^1$ is other than hydrogen with an acid or a base;

b. for compounds of formula (I) wherein $R^1$ is other than H:

reacting a compound of formula (II):

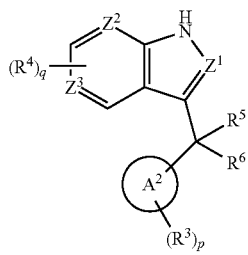

(II)

wherein $A^2$, $Z^1$, $Z^2$, $Z^3$, $R^3$, $R^4$, $R^5$, $R^6$, p and q are as defined in claim 1;

with a compound of formula (III):

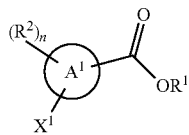

(III)

wherein $A^1$, $R^2$ and n are as defined in claim 1;

$R^1$ is $C_{1-6}$ alkyl optionally substituted with one or more substituents selected from the group consisting of halo, OH, and phenyl, wherein the phenyl group is optionally substituted with 1 to 3 substituents selected from the group consisting of OH, CN, $NO_2$, halo, $C_{1-4}$ alkyl, and $C_{1-4}$ haloalkyl; and $X^1$ is a leaving group; or c. for compounds of formula (I) wherein $R^5$ and $R^6$ together form a carbonyl group:

reacting a compound of formula (IX):

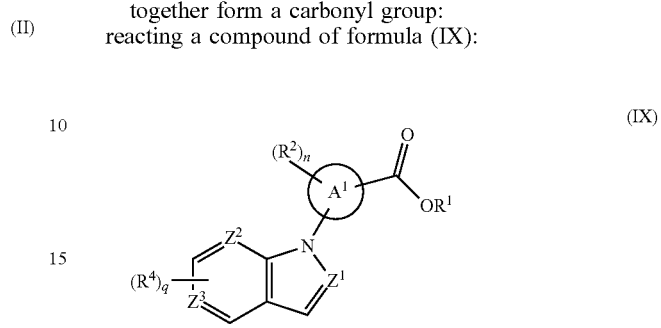

(IX)

wherein $A^1$, $Z^1$, $Z^2$, $Z^3$, $R^1$, $R^2$, $R^4$, n, and q are as defined in claim 1 with a compound of formula (X)

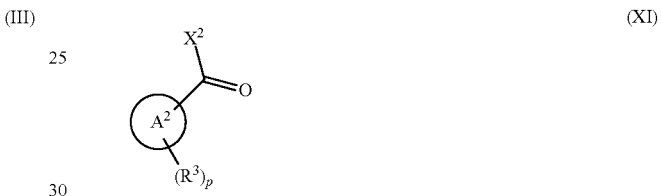

(XI)

wherein $A^2$, $R^3$ and p are as defined in claim 1 and $X^2$ is a leaving group.

* * * * *